United States Patent [19]
Yager et al.

[11] Patent Number: 5,932,100
[45] Date of Patent: Aug. 3, 1999

[54] MICROFABRICATED DIFFERENTIAL EXTRACTION DEVICE AND METHOD

[75] Inventors: Paul Yager; James P. Brody; Mark R. Holl; Fred K. Forster; Paul C. Galambos, all of Seattle, Wash.

[73] Assignee: University of Washington, Seattle, Wash.

[21] Appl. No.: 08/663,916

[22] Filed: Jun. 14, 1996

Related U.S. Application Data

[60] Provisional application No. 60/000,261, Jun. 16, 1995.
[51] Int. Cl.$^6$ .............................. B01D 11/00; B01D 11/04
[52] U.S. Cl. ........................ 210/634; 210/96.1; 210/511; 210/739; 210/748; 216/56; 422/55; 422/69; 436/178
[58] Field of Search ............................... 210/85, 94, 96.1, 210/511, 634, 739, 745, 748, 198.2, 243, 805; 422/69, 70, 101, 82.05, 82.08; 216/2, 56; 435/6, 287.1, 287.2, 287.3

[56] References Cited

U.S. PATENT DOCUMENTS

| | | | |
|---|---|---|---|
| 3,449,938 | 6/1969 | Giddings . | |
| 4,147,621 | 4/1979 | Giddings . | |
| 4,214,981 | 7/1980 | Giddings | 209/155 |
| 4,250,026 | 2/1981 | Giddings et al. | 209/155 |
| 4,726,929 | 2/1988 | Gropper et al. | 422/68 |

(List continued on next page.)

FOREIGN PATENT DOCUMENTS

| | | |
|---|---|---|
| 0 381 501 A2 | 8/1990 | European Pat. Off. . |
| 645169 | 3/1995 | European Pat. Off. . |
| WO93/22053 | 11/1993 | WIPO . |
| WO93/22054 | 11/1993 | WIPO . |
| WO93/22055 | 11/1993 | WIPO . |

(List continued on next page.)

OTHER PUBLICATIONS

Springston et al., "Continuous Particle Fractionation Based on Gravitational Sedimentation in Split–Flow Thin Cells," *Analytical Chemistry* (1987) 59:344–350.
Elwenspoek, M. et al., "Towards integrated microliquid handling systems," *J. Micromech. Microeng.* (1994) 4:227–245.
Afromowitz, M.A. and Samaras, J.E., "Pinch Field–Flow Fractionation Using Flow Injection Techniques," *Separation Science and Technology* (1989) 24 (5&6):325–339.
Faucheux, L.S., et al. (1995), "Optical Thermal Ratchet," *Physical Rev. Letters* 74(9):1504–1507.
Forster, F.K. et al., "Design, Fabrication and Testing of Fixed–Valve Micro–Pumps," ASME International Mechanical Engineering Congress & Exposition (1995), San Francisco, ASME.
Giddings, J.C. et al., "Outlet Stream Splitting for Sample Concentration in Field–Flow Fractionation," *Separation Science and Technology* (1983) 18(3):293–306.

(List continued on next page.)

*Primary Examiner*—Joseph W. Drodge
*Attorney, Agent, or Firm*—Greenlee, Winner and Sullivan, P.C.

[57] ABSTRACT

This invention provides a microfabricated extraction system and methods for extracting desired particles from a sample stream containing desired and undesired particles. The sample stream is placed in laminar flow contact with an extraction stream under conditions in which inertial effects are negligible. The contact between the two streams is maintained for a sufficient period of time to allow differential transport of the desired particles from the sample stream into the extraction stream. In a preferred embodiment the differential transport mechanism is diffusion. The extraction system of this invention coupled to a microfabricated diffusion-based mixing device and/or sensing device allows picoliter quantities of fluid to be processed or analyzed on devices no larger than silicon wafers.

38 Claims, 9 Drawing Sheets

U.S. PATENT DOCUMENTS

| | | | |
|---|---|---|---|
| 4,737,268 | 4/1988 | Giddings | 209/12 |
| 4,830,756 | 5/1989 | Giddings | 210/739 |
| 4,894,146 | 1/1990 | Giddings | 209/12 |
| 5,039,426 | 8/1991 | Giddings | 210/695 |
| 5,141,651 | 8/1992 | Giddings | 210/748 |
| 5,156,039 | 10/1992 | Giddings . | |
| 5,193,688 | 3/1993 | Giddings | 209/155 |
| 5,240,618 | 8/1993 | Caldwell et al. | 210/748 |
| 5,250,263 | 10/1993 | Manz | 422/81 |
| 5,288,463 | 2/1994 | Chemelli | 422/58 |
| 5,304,487 | 4/1994 | Wilding et al. | 435/291 |
| 5,322,626 | 6/1994 | Frank et al. | 210/634 |
| 5,465,849 | 11/1995 | Wada et al. | 209/214 |
| 5,480,614 | 1/1996 | Kamahori | 422/70 |
| 5,498,392 | 3/1996 | Wilding et al. | 422/68.1 |
| 5,549,819 | 8/1996 | Nickerson | 210/511 |
| 5,554,339 | 9/1996 | Cozzette et al. | 422/69 |
| 5,571,410 | 11/1996 | Swedberg et al. | 422/69 |
| 5,585,011 | 12/1996 | Saaski et al. | 216/56 |
| 5,585,069 | 12/1996 | Zanzucchi et al. | 422/100 |
| 5,587,128 | 12/1996 | Wilding et al. | 435/287.3 |
| 5,599,432 | 2/1997 | Manz et al. | 204/451 |
| 5,605,662 | 2/1997 | Heller et al. | 422/69 |
| 5,632,957 | 5/1997 | Heller et al. | 422/69 |
| 5,637,469 | 6/1997 | Wilding et al. | 435/287.2 |
| 5,639,423 | 6/1997 | Northrup et al. | 435/287.3 |
| 5,674,743 | 10/1997 | Ulmer | 435/287.2 |
| 5,681,484 | 10/1997 | Zanzucchi et al. | 216/56 |
| 5,707,799 | 1/1998 | Hansmann et al. | 435/6 |
| 5,726,751 | 3/1998 | Attendorf . | |
| 5,747,349 | 5/1998 | Van Den Engh . | |

FOREIGN PATENT DOCUMENTS

| | | |
|---|---|---|
| WO93/22058 | 11/1993 | WIPO . |
| WO93/22421 | 11/1993 | WIPO . |
| WO 96/12540 | 10/1995 | WIPO . |
| WO 96/12541 | 10/1995 | WIPO . |
| WO96/04547 | 2/1996 | WIPO . |
| WO96/15576 | 5/1996 | WIPO . |

OTHER PUBLICATIONS

Giddings, J.C., "Optimized Field–Flow Fractionation System Based on Dual Stream Splitters," *Anal. Chem.* (1985) 57:945–947.

Giddings, J.C., "Field–Flow Fractionation: Analysis of Macromolecular, Colloidal and Particulate Materials," *Science* (1993) 260:1456–1465.

Gravesen, P. et al., "Microfluidics—a review," *Micromechanics and Microengineering* (1993) 3(4):168–182.

Harrison, D.J. et al., "Micromachining a miniaturized capillary electrophoresis–based chemical analysis system on a chip," *Science* (1993) 261:895–897.

Kittilsand, G. and Stemme, G., "A Sub–micron Particle Filter in Silicon," *Sensors and Actuators* (1990) A21–A23:904–907.

Leff, H.S. and Rex, A.F., "Resource Letter MD–1: Maxwell's demon," *Am. J. Physics* (1990) 58(3):201–209.

Levin, S. and Tawil, G., "Analytical SPLITT Fractionation in the Diffusion Mode Operating as a Dialysis–like system Devoid of Membrane. Application to Drug–Carrying Liposomes," *Anal. Chem.* (1993) 65:2254–2261.

Manz, A. et al. "Electroosmotic pumping and electrophoretic separations for miniaturized chemical analysis system," *J. Micromech. Microeng.* (1994) 4:257–265.

Giddings, J. C. (1988), "Continuous Separation in Split–Flow Thin (SPLITT) Cells: Potential Applications to Biological Materials," *Sep. Sci Technol.* 23(8&9):931–943.

Fuh, C.B. et al. (1993), "Rapid Diffusion Coefficient Measurements Using Analytical SPLITT Fractionation: Application to Proteins," *Anal. Biochem.* 208:80–87.

Brody, J.P. and Yager, P. (1996), "Low Reynolds Number Micro–Fluidic Devices," Solid State Sensor & Actuator Workshop, Hilton Head, S.C., Jun. 2–6, 1996.

Manz (1993), "Planar Chips Technology for Miniaturization of Separation Systems: A Developing Perspective in Chemical Monitoring," Adv. Chromatrgr. 33:1–66.

Verpoorte, E.M. et al. (1994), "Three–dimensional microflow manifolds for miniaturized chemical analysis systems," J. Micromech. Microeng. 4:246–256.

Weigl, B.H and Yager, P. (1996), "Silicon–Microfabricated Diffusion–Based Optical Chemical Sensor," presented at the Europtrode Conf., Zurich, Switzerland, Apr. 2–3, 1996.

Ramsey, J.M. et al. "Microfabricated chemical measurement systems," *Nature Medicine* (1995) 1(10):1093–1096.

Rousselet, J., et al. "Directional motion of brownian particles induced by a periodic asymmetric potential," *Nature* (1994) 370:446–448.

Shoji, S. and Esashi, M. "Microflow devices and systems," *J. Micromechanics and Microengineering* (1994) 4:157–171.

Wallis, G. and Pomerantz, D.I., "Field assisted glass–metal sealing," *J. Applied Physics,* (1969) 40(10):3946–3949.

Wilding, P. et al., "Manipulation and Flow of Biological Fluids in Straight Channels Micromachined in Silicon," *J. Clin. Chem.* (1994) 40(1):43–47.

Williams, P.S. et al., "Continuous SPLITT Fractionation Based on a Diffusion Mechanism," *Ind. Eng. Chem. Res.* (1992) 31:2172–2181.

Yue, V. et al., "Miniature Field–Flow Fractionation Systems for Analysis of Blood Cells," *Clin. Chem.* (1994) 40:1810–1814.

MICROFABRICATED DIFFERENTIAL EXTRACTION DEVICE AND METHOD

CROSS-REFERENCE TO RELATED APPLICATIONS

This is a utility patent application taking priority from provisional patent application 60/000,261 filed Jun. 16, 1995, which is incorporated herein by reference.

This invention was made with government support under Army research contract DAMD17-94-J-4460 awarded by the U.S. Army. The government has certain rights in the invention.

FIELD OF THE INVENTION

This invention relates generally to microfabricated extraction systems and methods for separating analytes from streams containing other constituents by differential transport principles such as diffusion and applied fields. The invention is useful, for example, for processing blood to separate a stream containing smaller particles such as albumin molecules from a stream containing cells.

BACKGROUND OF THE INVENTION

Chemical analysis of biological samples is constrained by sample size. Withdrawing a few milliliters of blood from an adult may have little effect, but repeating this procedure every hour or even withdrawing this amount once from an infant can significantly alter the health of the subject. For these reasons, a miniaturized blood analysis system would be useful. Furthermore, while many sophisticated tests that have great importance for critical care can be performed in major hospital laboratories, a substantial impact could be made on the practice of emergency medicine if some key tests could be performed on the patient at the site of injury. For some assays it is vital to make measurements in the absence of red blood cells, so some form of separation of cells from plasma is required.

Diffusion is a process which can easily be neglected at large scales, but rapidly becomes important at the microscale. The average time t for a molecule to diffuse across a distance d is $2t=d^2/D$ where D is the diffusion coefficient of the molecule. For a protein or other large molecule, diffusion is relatively slow at the macroscale (e.g. hemoglobin with D equal to $7 \times 10^{-7}$ cm$^2$/s in water at room temperature takes about $10^6$ seconds (ten days) to diffuse across a one centimeter pipe, but about one second to diffuse across a 10 $\mu$m channel).

Using tools developed by the semiconductor industry to miniaturize electronics, it is possible to fabricate intricate fluid systems with channel sizes as small as a micron. These devices can be mass-produced inexpensively and are expected to soon be in widespread use for simple analytical tests. See, e.g., Ramsey, J. M. et al. (1995), "Microfabricated chemical measurement systems," Nature Medicine 1:1093–1096; and Harrison, D. J. et al (1993), "Micromachining a miniaturized capillary electrophoresis-based chemical analysis system on a chip," Science 261:895–897.

Miniaturization of analytic instruments is not a simple matter of reducing their size. At small scales different effects become important, rendering some processes inefficient and others useless. It is difficult to replicate smaller versions of some devices because of material or process limitations. For these reasons it is necessary to develop new methods for performing common laboratory tasks on the microscale.

Devices made by micromachining planar substrates have been made and used for chemical separation, analysis, and sensing. See, e.g., Manz, A. et al. (1994), "Electroosmotic pumping and electrophoretic separations for miniaturized chemical analysis system," J. Micromech. Microeng. 4:257–265.

Field flow fractionation devices involve particle size separation using a single inlet stream. See, e.g. Giddings, J. C., U.S. Pat. No. 3,449,938, Jun. 17, 1969, "Method for Separating and Detecting Fluid Materials"; Giddings, J. C., U.S. Pat. No. 4,147,621, Apr. 3, 1979, "Method and Apparatus for Flow Field-Flow Fractionation"; Giddings, J. C., U.S. Pat. No. 4,214,981, Jul. 29, 1980, "Steric Field-Flow Fractionation"; Giddings, J. C. et al., U.S. Pat. No. 4,250,026, Feb. 10, 1981, "Continuous Steric FFF Device for The Size Separation of Particles"; Giddings, J. C. et al. (1983), "Outlet Stream Splitting for Sample Concentration in Field-Flow Fractionation," Separation Science and Technology 18:293–306; Giddings, J. C. (1985), "Optimized Field-Flow Fractionation System Based on Dual Stream Splitters," Anal. Chem. 57:945–947; Giddings, J. C., U.S. Pat. No. 4,830,756, May 16, 1989, "High Speed Separation of Ultra-High Molecular Weight Polymers by Hyperlayer Field-Flow Fractionation"; Giddings, J. C., U.S. Pat. No. 4,141,651, Aug. 25, 1992, "Pinched Channel Inlet System for Reduced Relaxation Effects and Stopless Flow Injection in Field-Flow Fractionation"; Giddings, J. C., U.S. Pat. No. 5,156,039, Oct. 20, 1992, "Procedure for Determining the Size and Size Distribution of Particles Using Sedimentation Field-Flow Fractionation"; Giddings, J. C., U.S. Pat. No. 5,193,688, Mar. 16, 1993, "Method and Apparatus for Hydrodynamic Relaxation and Sample Concentration in Field-Flow Fraction Using Permeable Wall Elements"; Caldwell, K. D. et al., U.S. Pat. No. 5,240,618, Aug. 31, 1993, "Electrical Field-Flow Fractionation Using Redox Couple Added to Carrier Fluid"; Giddings, J. C. (1993), "Field-Flow Fractionation: Analysis of Macromolecular, Colloidal and Particulate Materials," Science 260:1456–1465; Wada, Y. et al., U.S. Pat. No. 5,465,849, Nov. 14, 1995, "Column and Method for Separating Particles in Accordance with Their Magnetic Susceptibility"; Yue, V. et al. (1994), "Miniature Field-Flow Fractionation Systems for Analysis of Blood Cells," Clin. Chem. 40:1810–1814; Afromowitz, M. A. and Samaras, J. E. (1989), "Pinch Field Flow Fractionation Using Flow Injection Techniques," Separation Science and Technology 24(5 and 6):325–339.

Thin-channel split flow fractionation (SPLITT) technology also provides particle separation in a separation cell having a thin channel. A field force is exerted in a direction perpendicular to the flow direction. Particles diffuse or are otherwise transported from a particle-containing stream across a transport stream to a particle-free stream. The device for operating the process is generally fabricated from glass plates with teflon sheets used as spacers to form the channels. The channel depth can therefore be no smaller than the spacers, which are generally about 100 to 120 $\mu$m thick. See, e.g., Giddings, J. C., U.S. Pat. No. 4,737,268, Apr. 12, 1988, "Thin Channel Split Flow Continuous Equilibrium Process and Apparatus for Particle Fractionation"; Giddings, J. C., U.S. Pat. No. 4,894,146, Jan. 16, 1990, "Thin Channel Split Flow Process and Apparatus for Particle Fractionation"; Giddings, J. C., U.S. Pat. No. 5,093,426, Aug. 13, 1991, "Process for Continuous Particle and Polymer Separation in Split-Flow Thin Cells Using Flow-Dependent Lift Forces"; Williams, P. S. et al. (1992), "Continuous SPLITT Fractionation Based on a Diffusion Mechanism," Ind. Eng. Chem. Res. 31:2172–2181; and Levin, S. and Tawil, G. (1993), "Analytical SPLITT Fractionation in the Diffusion Mode Operating as a Dialysis-like System Devoid of Membrane. Application to Drug-Carrying Liposomes," Anal. Chem. 65:2254–2261.

The object of this invention is to provide a microfabricated extraction system utilizing differential transport principles in which an analyte can be extracted, detected and quantified.

The advantages, as disclosed herein, of diffusion separation devices on the microscale, e.g., having channel depths no greater than about 100 μm, do not appear to have been recognized in the prior art. See, e.g., Kittilsand, G. and Stemme, G. (1990), Sensors and Actuators A21–A23:904–907, and Wilding, P. et al. (1994), J. Clin. Chem. 40:43–47.

All publications, patents and patent applications referred to herein are hereby incorporated by reference.

SUMMARY OF THE INVENTION

This invention provides an extraction method and device distinguished from conventional filtration techniques and devices in possessing advantages of size, production economy, integrability with micro chemical analysis systems, low power consumption, and which may be operated in either a sample-to-sample or continuous processing mode. The device is particularly well suited to integration with microfabricated chemical analysis systems in which, for example, a preferred embodiment provides a microfabricated extraction device or system capable of providing a diluted plasma product having a volume ranging from picoliters to nanoliters starting from samples as small as a microliter of whole blood, with a comparable extraction stream volume.

The extraction system is useful as an element in an integrated system of microfluidic and detection elements (such as optical detectors) for tests of medical interest on blood, and also has applications in many other areas of analytical chemistry. In a preferred embodiment useful for blood analysis, the device allows for the extraction of plasma constituents from whole blood, thereby producing a cell-free fluid stream for subsequent analysis.

The microfabricated extraction system of this invention in simplest concept is illustrated by a diffusion extraction device comprising microchannels in the shape of an "H". A mixture of particles suspended in a sample stream enters the extraction channel (the crossbar of the "H") from one of the arms, e.g. the top left, and an extraction stream (a dilution stream) enters from the bottom left. The two streams flow together in the extraction channel; however, due to the small size of the channels, the flow is laminar and the streams do not mix. The sample stream exits as by-product stream at the upper right and the extraction stream exits as product stream from the lower right. While the streams are in parallel laminar flow in the extraction channel, particles having a greater diffusion coefficient (smaller particles such as albumin, sugars and small ions) have time to diffuse into the extraction stream, while thee larger particles (e.g. blood cells) remain in the sample stream. Particles in the exiting extraction stream (now called the product stream) may be analyzed without interference from the larger particles.

In this patent application, the flow direction of a channel is called its length (L). The channel dimension in the direction of particle transport at right angles to the length (L) is called its depth (d). The third channel dimension at right angles to both the length and depth is called its width (w). The depth (d) is therefore perpendicular to the plane of interface of the sample and extraction streams. Table 1 lists other abbreviations used herein.

TABLE 1

| | |
|---|---|
| V | Volume |
| $V_{ss}$ | Sample stream flow rate (m³/s) |
| $V_{es}$ | Extraction stream flow rate (m³s) |
| $V_{ps}$ | Product stream flow rate (m³s) |
| $V_{bps}$ | By-product stream flow rate (m³s) |
| $V_{ind}$ | Indicator dye stream flow rate (m³s) |
| $V_{ds}$ | Detection stream flow rate (m³s) |
| $C_{i,ss}$ | Sample stream constituent i concentration (kg/kg) |
| $C_{i,es}$ | Extraction stream constituent i concentration (kg/kg) |
| $C_{i,bps}$ | By-product stream constituent i concentration (kg/kg) |
| $C_{i,ps}$ | Product stream constituent i concentration (kg/kg) |
| $C_{dye,ind}$ | Indicator stream dye concentration (kg/kg) |
| $C_{i,ds}$ | Detector stream constituent i concentration (kg/kg) |
| d | Diffusion direction extraction channel depth (m) |
| w | Extraction channel width (m) |
| L | Extraction channel length (m) |
| $a_\%$ | Percentage deviation from equilibrium concentration |
| $L_{a\%}$ | Device length required to achieve $a_\%$ (m) |
| $z_s$ | Interface streamline location between sample and extraction streams at the extraction channel entrance (m) |
| $z_p$ | Interface streamline location between the by-product and product streams (m) |
| P | Absolute pressure within the fluid stream (Pa) |
| Δp | Differential pressure between the entrance and exit of the extraction channel (Pa) |
| $D_i$ | Binary diffusion coefficient of constituent i (m²/s) |
| $\mu$ | Fluid viscosity (Pa.s) |
| $\rho$ | Fluid density (kg/m³) |
| $\xi$ | Equilibrium normalized constituent concentration for an infinite length extraction channel (dimensionless) |
| č | Normalized constituent concentration (dimensionless) |
| x | Channel length coordinate direction (flow direction) |
| y | Channel width coordinate direction |
| z | Diffusion direction coordinate |
| x, z | Non-dimensional normalized variables (dimensionless) |
| w/d | Aspect ratio |
| D | Diffusion coefficient |
| Re | Reynolds number |
| T | Temperature |
| u | Axial velocity |

The length of the extraction channel and the extraction channel flow velocity are key parameters determining the amount of time the particles have to diffuse into the extraction stream. The particles in the case described above are differentially transported from the sample stream to the extraction stream using diffusion as the transport mechanism. Other means for effecting differential transport of the desired particles can also be used. The term "differential transport" means that a portion of the desired particles are transported from the sample stream into the extraction stream to the substantial exclusion of the undesired particles. For example, magnetic, electrical or other forces can be applied across the extraction stream, temperature gradients can be used, or absorbent or adsorbent materials such as antibodies can be added to the extraction stream to capture the desired particles.

One preferred embodiment entails the incorporation in the extraction stream of an adsorbent material such as a receptor with specificity for the desired ligand particles, onto an effectively non-diffusing substrate, such as plastic beads or high molecular weight polymers. Another preferred embodiment utilizes an effectively non-diffusing absorbent particulate material with specificity for the desired particles. Such materials are considered "effectively non-diffusing" when they do not diffuse into the sample stream, or do not diffuse into the sample stream in quantities large enough to interfere with detection of the undesired particles in the by-product stream. In the absorbent embodiment, desired particles are absorbed within the effectively non-diffusing absorbing particulate material, whereas in the adsorbent embodiment, the desired particles attach to the surface of the effectively non-diffusing substrate plastic beads or to ligands attached thereto. Numerous suitable ligands for desired particles in the adsorbent/absorbent embodiment are known to the art, and specific teachings relative to these techniques are disclosed in co-pending application Ser. No. 08/876,038 [Attorney Docket No. 35-96P filed concurrently herewith.]

The microfabricated device of this invention for extracting desired particles from a sample stream containing said particles comprises:

a. a sample stream inlet;

b. an extraction stream inlet;

c. an extraction channel having an aspect ratio (channel width to depth) less than 50 in fluid communication with said sample stream inlet and said extraction stream inlet for receiving a sample stream from said sample stream inlet in parallel laminar flow with an extraction stream from said extraction stream inlet;

d. a by-product stream outlet in fluid communication with said extraction channel for receiving a by-product stream comprising at least a portion of said sample stream from which desired particles have been extracted;

e. a product stream outlet in fluid communication with said extraction channel for receiving a product stream comprising at least a portion of said extraction stream and comprising desired particles extracted from said sample stream.

The sample stream and extraction stream inlets and the by-product stream and product stream outlets may comprise channels, reservoirs, ports, or other containers. The sample stream inlet is designed to receive a sample stream containing "desired particles," i.e. particles it is desired to extract so that their presence may be detected. The sample stream also includes other particles which are not extracted, termed "undesired particles" herein. These undesired particles include particles which might interfere with the detection of the desired particles. In a preferred embodiment, the sample stream comprises whole blood. The desired particles may be albumin or other blood plasma components, and the undesired particles are blood cells. The device is especially useful for obtaining cell-free plasma from whole blood. Other fluids for which the present invention is useful include solutions or suspensions of DNA fragments of different lengths, or proteins of varying sizes. Sample streams useful in the practice of this invention include fermentation broths, raw sewage, liquefied food samples, soil samples and biological fluids such as sputum, urine, and cerebral spinal fluid.

The term "particles" refers to molecules, cells, large molecules such as proteins, small molecules comprised of one or several atoms, and ions. The particles may be suspended or dissolved in the stream. The term "stream" refers to a carrier fluid such as water or other liquid, air or other gas, containing desired and/or undesired particles. The term "particles" as used herein does not include the molecules of the carrier stream.

The term "extraction" refers to the separation of at least a portion, i.e. a detectable portion, of desired particles from the sample stream to the substantial exclusion of undesired particles. It is recognized that very small amounts of undesired particles may be transported into the extraction stream; however, the presence of such undesired particles will be minimized such that they do not interfere with detection or subsequent processing of the streams containing the desired particles.

The term "laminar flow" of two streams means stable, side-by-side, non-recirculating, flow of two streams without mixing. There are no zones of recirculation, and turbulence is negligible. As is known to the art, the Reynolds number of a flow is the ratio of inertial forces to viscous forces. For flow through a duct, the Reynolds number is calculated using the equation $Re = \rho d(v/\mu)$ where Re is the Reynolds number, $\rho$ is the mass density of the fluid, d is a typical cross-sectional dimension of the duct depending on the shape of the duct, v is the mean velocity over the duct cross-section and $\mu$ is the viscosity.

As the Reynolds number is reduced, flow patterns depend more on viscous effects and less on inertial effects. Below a certain Reynolds number (based on lumen size for a system of channels with bends and lumen size changes), inertial effects are insufficient to cause phenomena indicative of their significant presence such as laminar recirculation zones and turbulent flow. Therefore, non-turbulent, laminar non-recirculating flow occurs in the extraction devices discussed herein. In such devices minimal dispersive mixing occurs as a result of the viscous flow velocity profiles present within any laminar viscous flow. This allows two laminar non-recirculating fluid streams to flow down an extraction channel for the purpose of desired particle extraction from one stream to the other.

The streams may be separated at the end of the conduit at any arbitrary location by precise regulation of the exit flow rate of the outlets, something which is not possible at higher Reynolds numbers not satisfying the non-recirculating and non-turbulent criteria.

The extraction stream inlet is designed to receive an extraction stream capable of accepting desired particles when in laminar flow contact with the sample stream. The extraction stream can be any fluid capable of accepting particles being transported from the sample stream. Preferred extraction streams are water and isotonic solutions such as physiological saline. Other useful extractant streams comprise organic solvents such as acetone, isopropyl alcohol, supercritical carbon dioxide or ethanol. Air and other gases may also be used as sample and extraction streams.

The by-product stream comprises the sample stream from which a portion of the desired particles have been extracted and may or may not, as discussed below, be comprised of a fraction of the extraction stream into which desired particles have been conveyed from the sample stream.

The by-product stream outlet is designed to conduct the by-product stream (composed of the sample stream and perhaps a portion of the extraction stream) that is removed from the extraction channel to disposal, recycle, or other system component, for further processing.

The product stream comprises at least a portion of the extraction stream into which desired particles have been extracted. The product stream outlet, which as stated above, may comprise a product stream channel, is designed to conduct the product stream containing a detectable quantity of desired particles to a detection or further processing area or system component. A sufficient quantity of the extraction stream must be present in the product stream, comprising a sufficient quantity of desired particles, such that the presence of the desired particles is detectable in the product stream by means known to the art.

The product stream may be conducted to a reservoir chamber, or other device where it may be further treated, e.g. by mixing, separating, analyzing, heating or otherwise processing, for example as disclosed in Wilding, P., et al. U.S. Pat. No. 5,304,487 issued Apr. 19, 1994, incorporated herein by reference.

The term "microfabricated" refers to devices capable of being fabricated on silicon wafers readily available to those practicing the art of silicon microfabrication and having the feature sizes and geometries producible by such methods as LIGA, thermoplastic micropattern transfer, resin based microcasting, micromolding in capillaries (MIMIC), wet isotropic and anisotropic etching, laser assisted chemical etching (LACE), and reactive ion etching (RIE), or other techniques known within the art of microfabrication. In the case of silicon microfabrication, larger wafers will accommodate a plurality of the devices of this invention in a plurality of configurations. A few standard wafer sizes are 3", 4", 6", and 8". Application of the principles presented herein using new and emerging microfabrication methods is within the scope and intent of the claims hereof.

The sample stream inlet and the extraction stream inlet need only be sized large enough to conduct the sample and extraction streams into parallel laminar flow, e.g., may comprise channels less than or equal to about 5 mm in length, less than about 100 micrometers in depth and less than or equal to 5 mm in width. The by-product exit and product outlets may similarly be minimal in size, comprising channels with dimensions as stated above for the sample, or extraction stream inlet. These inlets and outlets may be as long, deep and wide as required by the system of which they are a part, however, they preferably have a volume less than about 2.5 microliters to accommodate small sample sizes.

The extraction channel receives the inflow of the sample and extraction streams from the sample and extraction stream inlets and conducts these streams in parallel laminar flow for a distance sufficient to allow extraction of the desired particles into the extraction stream.

The width and depth of the sample stream inlet channel, extraction channel and by-product exit must be large enough to allow passage of the undesired particles, preferably anywhere between about 2 or 3 times the diameter of the undesired particles in the sample stream and less than or equal to about 5 mm. Particle sizes range from one or a few Å for small organic and inorganic molecules and ions to about 0.01 micrometers in depth for proteins, to about 0.1–1 micrometers for flexible long-chained molecules, to about 8 micrometers for red blood cells, to about 15 micrometers for most white blood cells, and up to about 25 micrometers for some white blood cells. The extraction channel must additionally be large enough to allow passage of particles used in the extraction stream such as adsorbent or absorbent particles, and is preferably between about 2 or 3 times the diameter of such particles and less than or equal to 5 mm. The extraction channel is most preferably less than 100 micrometers in order to achieve particle transport in a reasonable period of time.

The width and depth of the extraction stream channel and product outlet channels must be large enough to allow passage of the desired particles, and any other particles associated with them, such as adsorbent or absorbent particles, and is preferably between about 2 or 3 times the diameter of any absorbent or adsorbent particles present in the extraction and by-product streams and less than or equal to 5 mm.

If the width dimension is in the wafer thickness direction, then for the silicon microfabricated embodiments of the microscale extraction devices of the present invention, the width of the sample, extraction, product, and by-product channels, inlets and outlets is less than the silicon wafer thickness, i.e. about 300 micrometers.

If the depth dimension is in the wafer thickness direction then for the silicon microfabricated embodiments of the microscale extraction devices of the present invention, the depth of the sample, extraction, product, and by-product channels, inlets and exits is less than the silicon wafer thickness, i.e. about 300 micrometers. Preferably the depth, particularly of the extraction channel, is less than about 200 micrometers, and more preferably less than about 100 micrometers.

In a preferred embodiment, in the "H" design, the inlet and outlet channels are between about 2 to 3 times the maximum-sized stream particulate diameter and about 100 micrometers in width and between about 2 to 3 times the diameter of the maximum-sized particles and less than about 100 micrometers in depth, and the extraction channel is between about 2 to 3 times the diameter of the maximum-sized particles and about ⅔ the wafer thickness in width, between about 2 to 3 times the diameter of the maximum-sized particles and less than about 100 micrometers in depth, and between about 4 and about 10 times the diameter of the maximum-sized particles and less than or equal to 5 mm long.

In a second embodiment in which the particle transport direction is rotated 90 degrees from that of the "H" design, called the "flat extraction device" herein, the inlet channels have a width equal to the extraction channel width at the entrance to the extraction channel of preferably between 2 and 3 particle diameters and about 500 micrometers, and the extraction channel is preferably between about 2 and 3 times the diameter of maximum-sized particles and less than or equal to 5 mm in width, between about 2 and 3 times the diameter of the maximum-sized particles and less than about 100 micrometers in depth, and between about 4 and about 10 times the diameter of the maximum-sized particles and less than or equal to 5 mm long.

The term "aspect ratio" as used herein refers to the ratio of the width to the depth of a channel.

The extraction channels of this invention have an aspect ratio less than 50. The aspect ratio may be less than 25 or any number from less than 1 to 49. Microfabricated devices of this invention which can be manufactured with extraction channels having aspect ratios less than 50 and having depths less than 100 micrometers have numerous advantages over similar constructions with larger aspect ratios and larger extraction channel depths. Motive forces on particles capable of effecting differential transport of desired particles within the extraction channel are the result of local field gradients. Ultra-small transport distances enable differential transport of desired particles faster than undesired particles in short periods of time, allowing for significant minimization of the size needed for the device at moderate extraction channel flow rates. In addition lower flow rates can be used.

Devices within the size range described above yield distinctive advantages when evaluated in the following performance categories: (a) power consumption to achieve objective, (b) size of device required to achieve the objective, and (c) integrability of devices in a plurality of systems for management and processing of very small fluid volumes in a batch (sample to sample) mode.

Some fields known to the art which may be used for differential transport of the particles in the devices of this invention are those produced by:

Sedimentation
Electrical energy
Temperature gradients
Cross Flow
Dielectrical gradients
Shear forces
Magnetic forces
Concentration gradients Means for producing such fields are known to the art in connection with mesoscale and macroscale devices.

Because of the small sizes of the channels described herein, differential transport of desired particles by diffusion or other means occurs extremely rapidly, e.g. within less than about 300 seconds, and if desired, less than about one second. Devices according to this invention can be fabricated which will detect the presence or determine the concentration of desired or undesired particles in the product and/or by-product streams where these particles occur in less than five minutes, or if desired in less than four minutes, or less than three minutes, or less than two minutes, or less than one minute, or less than ten seconds, or less than one second.

In the microfabricated devices of this invention in comparison to the larger-scale devices of the prior art having channel depths greater than 100 micrometers, samples of much smaller size, e.g. about 1 mL, and down to about 1 picoliter, may be treated, whereas in larger devices, very small samples could be absorbed onto the channel walls. In addition, low Reynolds numbers for the flow are achieved, allowing for laminar flow and minimizing or totally eliminating turbulence which would interfere with differential extraction of desired particles.

A portion of the desired particles in the sample stream (having larger diffusion coefficients than the undesired particles, or being more susceptible than the undesired particles to transport into the extraction stream when differential transport means are applied to the system) is transported to the product stream. When the extraction is diffusion-based, some of the smaller particles will always remain in the sample stream; however, the percentage of desired particles transported to the product stream can be increased by increasing the time of contact of the sample and extraction streams, e.g. by increasing the length of the extraction channel or reducing the flow velocity. For simple diffusion systems, the process may be timed such that the two streams are in contact up to the point where the concentration of smaller particles in both streams is almost equal.

The sample and extraction streams may have different properties e.g. viscosities, densities, surface energies, diffusion coefficients, homogeneities, chemical compositions and the like, which may affect the differential transport rates. System parameters may need to be adjusted and optimized to take account of these differing properties, as will be apparent to those skilled in the art.

The sample and extraction streams are kept in contact in the extraction channel for a period of time sufficient to allow an analyzable quantity of desired particles to be transported into the extraction stream. The amount of product recovered from the device may be between about 0.001 picoliter/sec and about 50 microliters/sec or more. For example, illustrated herein is an optimal flow rate for the product stream of about 200 nanoliters/sec. As is known in the art, even the very small amounts of analytes present in such small product streams may be detected by spectroscopic and other means.

Successful operation of the invention described herein requires precise control of volume flow rates on three of the four channels of the device (i.e. sample, extraction, product, and by-product streams). The fourth channel need not and should not be regulated, as leaving this channel unregulated will allow the device to accommodate unpredictable changes in volume of the sample because of $\Delta V$ of mixing of the sample and extraction streams. Means for achieving precisely regulated flow rates are known to the art.

To aid in controlling the size of particles being transported to the product stream in a diffusion-based extraction system of this invention, and reduce the appearance of larger particles in the product stream, a fluid barrier may be created in the extraction channel. Such a fluid barrier is present when the extraction stream is present in sufficient volume to cause a portion of the extraction stream to flow through the by-product exit with the exiting by-product stream, as illustrated in FIG. 3. Smaller particles diffusing into the extraction stream must cross the width of this fluid barrier before being able to exit with the product stream. Such fluid barriers formed on a larger scale are discussed in Williams P. S., et al. (1992), "Continuous SPLITT Fractionation Based on a Diffusion Mechanism," Ind. Eng. Chem. Res. 2172–2181, incorporated herein by reference.

By controlling the pressure of the sample and extraction streams, the ratio of volume from each that enters the extraction channel can be controlled. The volume ratio of the sample stream and the extraction stream can also be set by the geometry of the outlet and inlet channels for a fixed delivery pressure on the sample and extraction streams. The volume flow rate of the product and by-product streams may also be controlled by manipulating the product and by-product stream pressures or by using arbitrary port (inlet) pressures and altering the flow resistance of the inlets. Whatever the control mode, the inlet and outlet channels must satisfy the criteria for minimum channel dimensions based on the size of the particulate to be processed as described above. If the volume of the extraction stream entering the extraction channel is greater than the volume of the sample stream, and the two exit streams are identical, a fluid barrier is formed. If the volume flow rate of the product stream is too small to accommodate the entire volume flow of the extraction stream then a fluid barrier will also be formed.

Extraction devices of this invention may comprise means for controlling the volume of extraction stream in the extraction channel with respect to the volume of the sample stream, which means include a product stream outlet smaller than required to allow the entire extraction stream to exit coupled with a by-product stream outlet large enough to handle the excess extraction stream. Extraction devices of this invention may comprise multiple product stream outlets so that product streams comprising different types of desired particles may be recovered.

The devices of this invention may be utilized as a sample pretreatment system for an analytical system including sensing means for detecting desired particles in the product stream. Such means include means for mixing the product stream with an indicator stream which interacts with the desired particles so as to allow them to be detected by sensing means known to the art, including optical means, such as optical spectroscopic equipment, and other means such as absorption spectroscopic equipment or means for detecting fluorescence, chemical indicators which change color or other properties when exposed to the desired particles of analyte, immunological means, electrical means, e.g. electrodes inserted into the device, electrochemical means, radioactive means, or virtually any microanalytical technique known to the art including magnetic resonance equipment or other means known to the art to detect the presence of analyte particles such as ions, molecules, polymers, viruses, DNA sequences, antigens, microorganisms, or other factors. Preferably, optical or fluorescent means are used, and antibodies, DNA sequences and the like are attached to fluorescent markers. Indicators and microfabricated mixing means, as well as detection and sensing means are described, e.g in copending application Ser. No. 08/625,808, now U.S. Pat. No. 5,716,852, incorporated herein by reference.

In a preferred embodiment of this invention the differential extraction device described above is integrated into an analytical system comprising means for further processing the product and/or by-product streams, such as diffusion-based mixing devices for mixing the product stream with an indicator substance (e.g. as described in copending application Ser. No. 08/625,808, now U.S. Pat. No. 5,716,852 incorporated herein by reference), and detection chambers wherein the presence of desired analyte particles may be detected. These additional processing means are preferably incorporated with the differential extraction device in a "lab-on-a-chip", fabricated on a standard silicon wafer. In a preferred embodiment, the system comprises quantitation means for determining the concentration of the analyte particles (desired or undesired particles) in the product and/or by-product stream and/or determining the concentration of the analyte particles in the sample stream. Such means include spectroscopic equipment, potentiometric, amperometric, and dielectric relaxation equipment. Concentration determinations can be made by calculation or calibration by means known to the art and disclosed herein.

The differential extraction devices of this invention are used in a method for extraction of at least a portion of desired particles from a sample stream comprising said desired particles and also containing undesired particles, comprising:

a. introducing said sample stream into the sample stream inlet of a microfabricated extraction device as described above;

b. introducing an extraction stream into the extraction channel of said extraction device; and c. withdrawing a product stream comprising desired particles from the product stream outlet of said device.

The method is performed in either batch or continuous mode operation. In batch mode, sample sizes may be as small as about one picoliter, preferably no more than about 250 microliters and more preferably are no more than about 50 microliters, although sample sizes of up to 1 mL or 10 mL or greater are also contemplated. The method is completed in a time period from less than 1 second to no more than about 5 minutes, although, again, the device can be fabricated to allow batch processing times of 10, 30, or 45 seconds, or 1, 2, 3 or 4 minutes, or less.

The batch method includes a start-up transition period wherein the fluid (which may be a gas) present within the extraction device is displaced by the extraction and sample streams as they enter the extraction channel until such time as the sample and extraction streams exist in a nearly equilibrium mass transport state.

An extraction period follows during which time the sample and extraction streams are in contact in the extraction channel for a period of time sufficient to allow sufficient desired particles to be differentially transported into the extraction stream for analysis or further processing.

A shut-down device flush period then may be required during which a cleansing fluid such as water (or soap solution) or air or sequential combinations of water (or soap solution) and air is cycled through the device to remove both desired and undesired particles which may have been retained on the surface of the device.

The batch method of this invention which involves processing of one single, discrete sample at a time, may include recycle of the by-product stream into the sample stream inlet and repetition of the process to increase the amount of desired particles removed from the original sample. In this embodiment a sample of the undesired particles is generated which may be useful for subsequent analysis. The processes of this invention can be repeated until the desired particles have been substantially completely extracted from the sample stream.

In the continuous mode of this invention, the process may be continued for periods greater than 5 minutes. Multiple devices of this invention can be arranged in series for the continuous mode so that the by-product stream from each device becomes the incoming sample stream to the next. This continuous application of the described devices produces as a result a series of finely regulated dilutions of the desired particles as well as a substantially clean stream of undesired particles upon exit from the last device of the series. In such an embodiment, the clean undesired particle by-product stream may also be routed to detection elements of the type mentioned above or to particulate sorting devices, counters, or sizing elements, such as a Si microfabricated flow cytometer, e.g. a silicon-based V-groove flow cytometer as described in U.S. patent application Ser. No. 08/534,515 filed Sept. 27, 1995, now U.S. Pat. No. 5,726,751; and 08/621,170 filed Mar. 20, 1996, now U.S. Pat. No. 5,747,349, the subject matter of each application incorporated herein by reference, or for further use. For example, in continuous mode, the devices of this invention may be used for dialysis, and the clear plasma stream recycled to a patient's body.

DETAILED DESCRIPTION OF THE PREFERRED EMBODIMENTS

Diffusion of small molecules occurs rapidly over typical microfabricated dimensions. The relationship between the size of a particle, ra, the diffusion coefficient, D, and temperature, T, is due to Einstein and for the simplest case, spherical particles, this can be written as:

$$D = \frac{k_b T}{6\pi\mu r_a}. \quad (1)$$

The characteristic distance, l, which a particle with diffusion coefficient D will diffuse in time, t, is $$l = \sqrt{Dt}. \quad (2)$$

Table 2 gives some typical diffusion coefficients and characteristic times.

TABLE 2

Some typical values for different sized particles and molecules. The characteristic time to diffuse 10 µm is given.

| Particle | D (20° C.) | t |
|---|---|---|
| 0.5 µm sphere | $5 \times 10^{-9}$ cm$^2$/sec | 200 sec |
| Protein (hemoglobin) | $7 \times 10^{-7}$ cm$^2$/sec | 1 sec |
| Small Molecule (fluorescein) | $5 \times 10^{-6}$ cm$^2$/sec | 0.2 sec |

Figure 1:
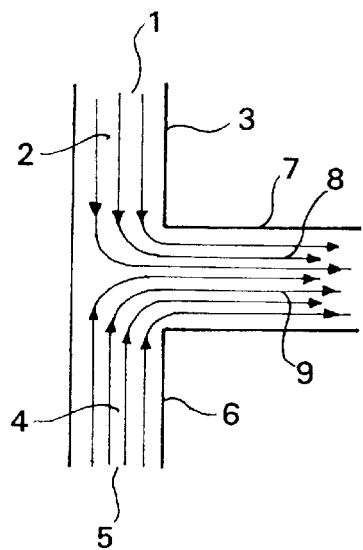
FIG. 1 shows a microchannel configuration showing laminar flow of two input streams having a low Reynolds number.

As shown in FIG. 1, in microchannels of small enough dimensions, inertial effects are negligible, such that a sample stream 2 entering a sample stream inlet 1 can flow from a sample stream channel 3 into an extraction channel 7 without mixing with an extraction stream 4 entering an extraction stream inlet 5 and flowing from an extraction stream inlet channel 6 into extraction channel 7. The two streams in the extraction channel 7 form a laminar sample stream 8 and a laminar extraction stream 9.

Figure 2:
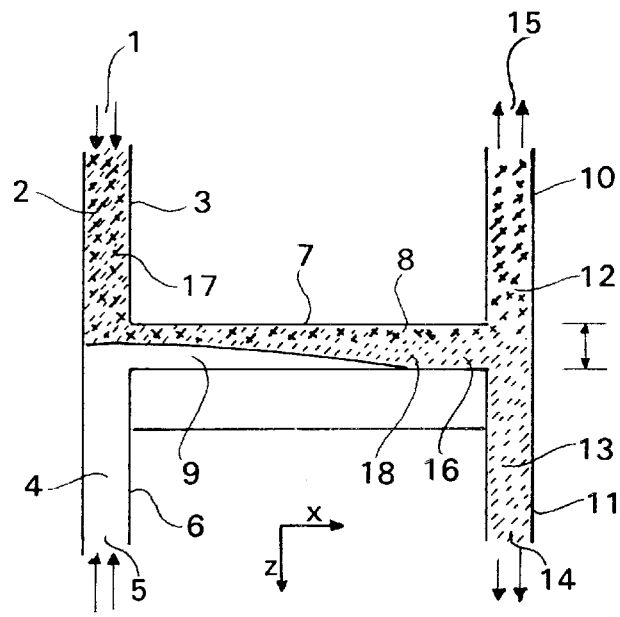
FIG. 2 shows a microchannel configuration illustrating the diffusion of smaller particles from a sample stream into a extraction stream.

In FIG. 2, the arrows at the upper left show the direction of flow in sample stream channel 3 of sample stream 2 entering sample stream inlet 1, and the arrows at the lower left show the direction of flow in extraction stream inlet channel 6 of extraction stream 4 entering extraction stream inlet 5. Sample stream 2 contains larger ("undesired") particles 17 and smaller ("desired") particles 18 (shown by cross-hatching). The sample stream 2 and extraction stream 4 come together in laminar flow in extraction channel 7 to form laminar sample stream 8 and laminar extraction stream 9 and the smaller desired particles 18 begin to diffuse from laminar sample stream 8 into laminar extraction stream 9 to form laminar product stream 16 which contains diffused smaller desired particles 18. The laminar sample stream 8 flows into by-product outlet channel 10 to form by-product stream 12, and leaves the channel through by-product outlet 15. The laminar extraction stream 9 receives smaller desired particles 18 diffused from laminar sample stream 8 and becomes laminar product stream 16 which in product outlet channel 11 becomes product stream 13 and leaves the channel through product outlet 14.

Figure 3:
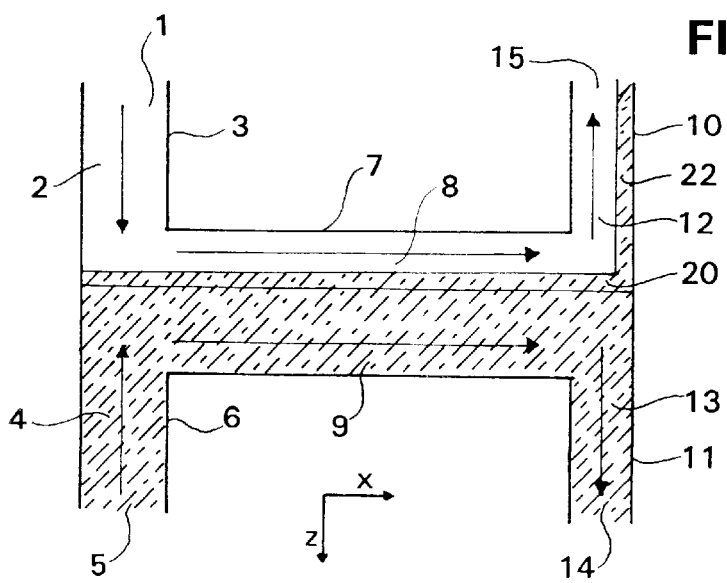
FIG. 3 shows a microchannel configuration illustrating the formation of a fluid barrier between a sample stream and a extraction stream.

In FIG. 3, the direction of the arrow at the upper left shows the direction of flow in sample stream channel 3 of sample stream 2 entering through sample stream inlet 1. The direction of the arrow at the lower left shows the direction of flow in extraction stream inlet channel 6 of extraction stream 4 entering through extraction stream inlet 5. Extraction stream 4 is indicated by cross-hatching. The upper arrow in extraction channel 7 shows the direction of flow of laminar sample stream 8 and the lower arrow in extraction channel 7 shows direction of flow of laminar extraction stream 9. When the volume of extraction stream 4 is greater than the amount which can exit through product outlet channel 11 and product outlet 14, part of laminar extraction stream 9 exits through by-product outlet channel 10 and by-product outlet 15 as excess extraction stream 22. This excess extraction stream 22 is in laminar flow in extraction channel 7 and forms fluid barrier 20. Smaller desired particles 18 (not shown in FIG. 3; see FIG. 2) in the sample stream 2 diffuse from laminar sample stream 8 through fluid barrier 20 into laminar extraction stream 9 to form product stream 16 (not shown in FIG. 3; see FIG. 2).

Figure 4:
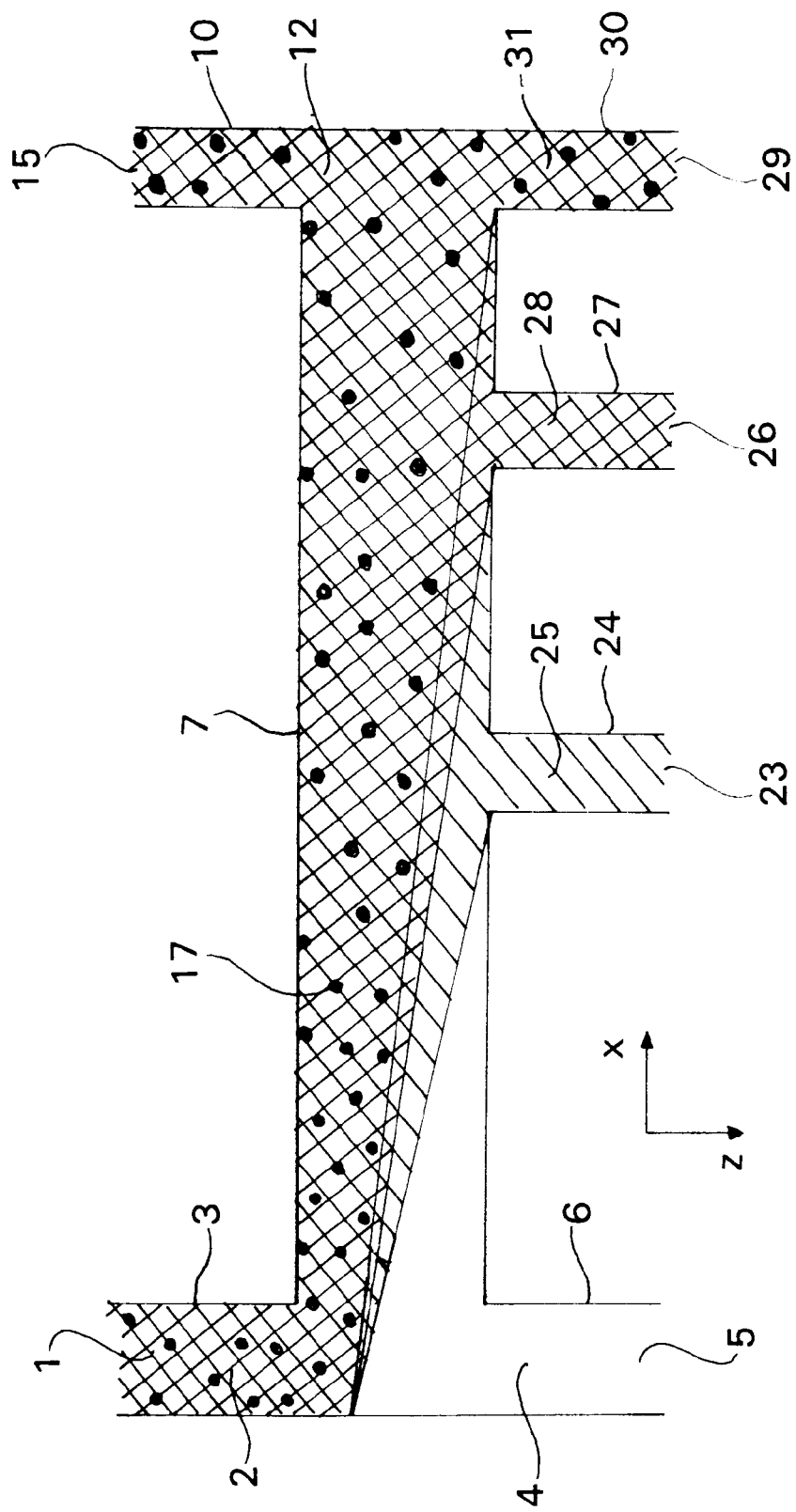
FIG. 4 shows a microchannel configuration (not to scale) illustrating an embodiment of this invention having multiple product channels to separate different sized particles. Black circles represent the largest particle sizes. Diagonal lines running from upper left to lower right represent medium sized particles, and diagonal lines running from lower left to upper right represent the smallest sized particles.

In FIG. 4 another embodiment of the invention is shown. A sample stream 2 containing large particles (black dots), medium-sized particles (diagonal lines from upper left to lower right), and small particles (diagonal lines from lower left to upper right) enters sample stream inlet 1. An extraction stream 4 enters extraction stream inlet 5 and flows to meet sample stream 2 in extraction channel 7. Small particles with larger diffusion coefficients which diffuse most rapidly exit first product outlet 23 in first exiting product stream 25 flowing through first product outlet channel 24 which is placed closest to the sample stream inlet 1. Medium-sized particles with medium-range diffusion coefficients exit along with small particles through second product outlet 26 in second exiting product stream 28 through second product outlet channel 27 placed further from sample stream inlet 1 than first product outlet channel 24 so as to allow more time for medium-sized particles to diffuse into the extraction stream. Large particles which have smaller diffusion coefficients and which diffuse more slowly exit third product outlet 29 in third exiting product stream 31 through third product outlet channel 30, along with small and medium-sized particles. The by-product stream 12 in feed exit channel 10 exiting through by-product outlet 15 also contains particles of all three sizes.

Figure 5:
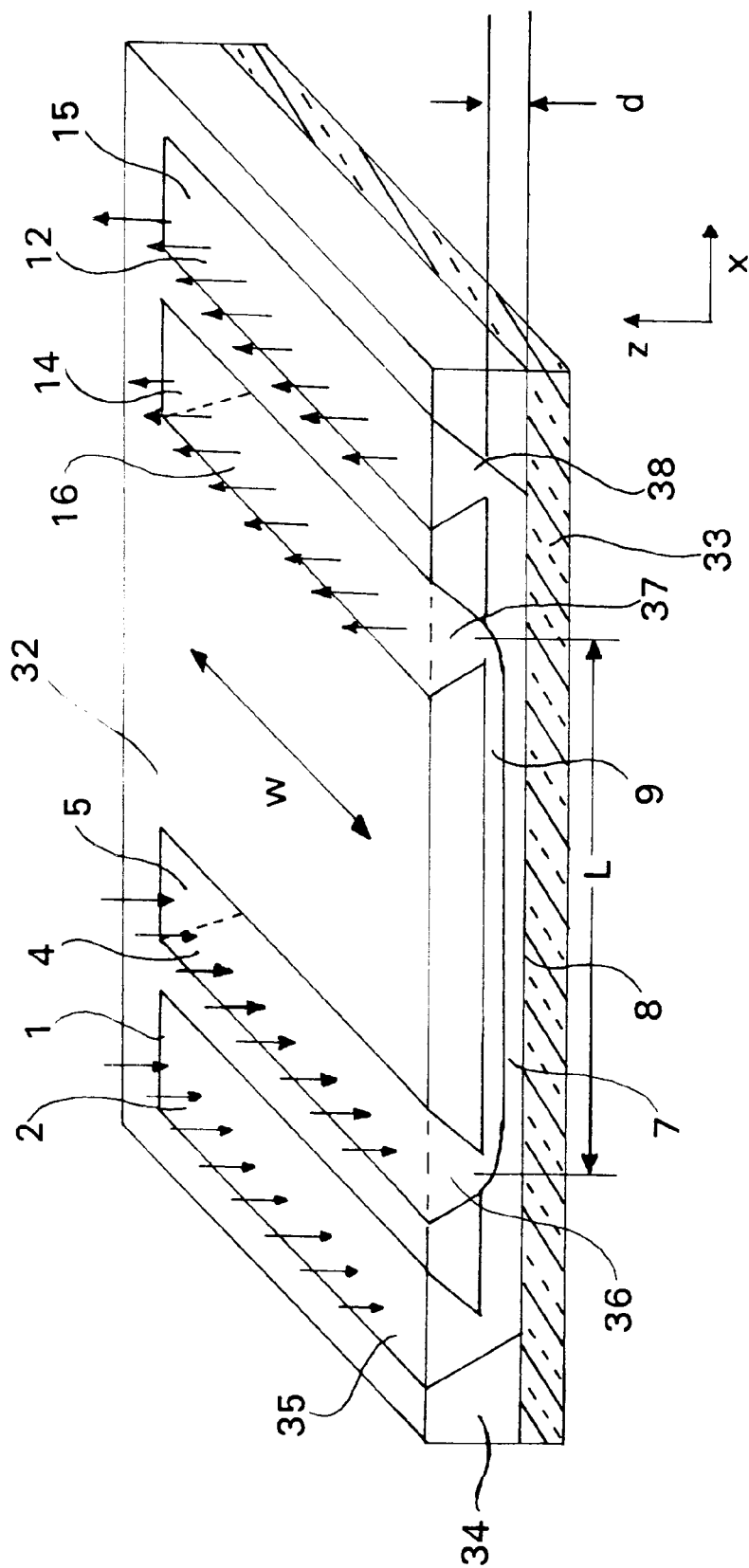
FIG. 5 shows a perspective view of microfabricated flat diffusion extraction system design with the diffusion direction rotated 90° from the "H" design shown in FIGS. 1–4.
Figure 6:
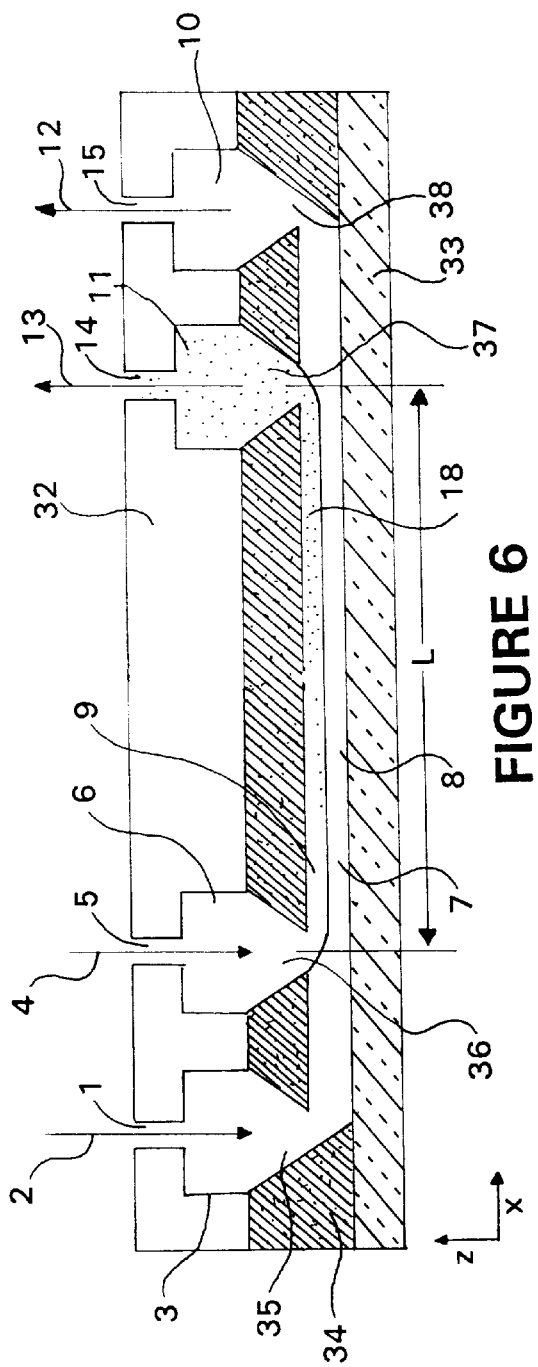
FIG. 6 shows a plan view of the microfabricated flat diffusion extraction system design of FIG. 5.

FIG. 5 shows a perspective view and FIG. 6 shows a plan view of a further embodiment of the invention, a "flat extraction device," in which the diffusion direction in extraction channel 7 is rotated 90° from the embodiments shown in FIGS. 1–4. This embodiment provides the advantage that the volume of material which can be processed is no longer limited by the with of the extraction channel 7.

The flat extraction device of FIGS. 5 and 6 is made by etching a silicon substrate 34 to provide sample stream inlet groove 35, extraction stream inlet groove 36, product stream exit groove 37, and by-product stream exit groove 38, as well as extraction channel 7. A glass cover 33 serves to enclose extraction channel 7. In FIG. 5, the arrows shown pointing downward into sample stream inlet 1 indicate the flow of sample stream 1. Similarly, the arrows pointing down into extraction stream inlet 5 indicate the flow of extraction stream 4. The arrows pointing up from product outlet 14 indicate the flow of product stream 16, and the arrows pointing up from by-product outlet 15 indicate the flow of by-product stream 12. The length of extraction channel 7 is shown as L and the width of the channels is indicated by the dark arrow as w. The depth of the extraction channel 7 is shown as d. A coupling manifold 32 shown in FIG. 6 with openings extends the depth of sample stream inlet groove 35 to form sample stream channel 3 and sample stream inlet 1, extends the depth of extraction stream inlet groove 36 to form extraction stream channel 6 and extraction stream inlet 5, extends the depth of product stream exit groove 37 to form product outlet channel 11 and product outlet 14, and extends the depth of by-product stream exit groove 38 to form by-product outlet channel 10 and by-product exit 15.

In the flat extraction system design shown in FIG. 6 operating by diffusion (concentration gradient) a sample stream 2 shown by the arrow in the upper left enters sample stream inlet 1 and flows in sample stream channel 3. Extraction stream 4 is indicated by an arrow entering extraction stream inlet 5, and flows in extraction stream inlet channel 6. Sample stream 2 flows as a laminar sample stream 8 in extraction channel 7 beneath laminar extraction stream 9. Laminar sample stream 8 is in contact with laminar extraction stream 9 in extraction channel 7 for a length L. Smaller ("desired") particles from laminar sample stream 8 indicated by the stippling in laminar extraction stream 9 flow into product outlet channel 11 as product stream 13 which exits at product outlet 14 as shown by the upward-pointing arrow. By-product stream 12 is the continuation of laminar sample stream 8 past product stream 13 which contains both the larger ("undesired") particles and a portion of the smaller ("desired") particles which have not diffused into product stream 13. By-product stream 12 flows through by-product outlet channel 10 out through by-product outlet 15.

By adjusting the configuration of the channels in accordance with the principles discussed herein to provide an appropriate channel length, flow velocity and contact time between the sample stream and the extraction stream, the size of the particles remaining in the sample stream and diffusing into the product stream can be controlled. The contact time required can be calculated as a function of the diffusion coefficient of the particle D (which generally varies as the linear size of a particle), and the distance d over which the particle must diffuse by $t=d^2/D$. Particles or molecules that have diffusion coefficients larger than D will be in the exiting product stream, and particles or molecules having a diffusion coefficient substantially smaller than D will not. If the diffusion coefficient of the larger particles being separated is about ten times smaller than D, the product should be almost entirely free of the large particles.

A simple calculation shows that few particles or molecules with diffusion coefficients smaller than $D=w_{fb}^2 v/L$ will be found in the exiting product stream, where $w_{fb}$ is the width of the fluid barrier, v is the mean flow velocity of the laminar sample stream and L is the length of the extraction channel. Particles or molecules with diffusion coefficients larger than $D=w^2 v/L$, where w is the width of the extraction channel, will be in the exiting product stream in the same concentration as in the by-product stream.

Means for injecting feed liquid into the device are provided, as when the device of this invention is used as part of an analytical system. Such means include standard syringes and tubes. Means for removing fluid from the product exit may also be provided, including receptacles for the fluid, inducing flow by capillary attraction, pressure, gravity, and other means known to the art as described above. Such receptacles may be part of an analytical or other device for further processing the product stream.

Figure 7:
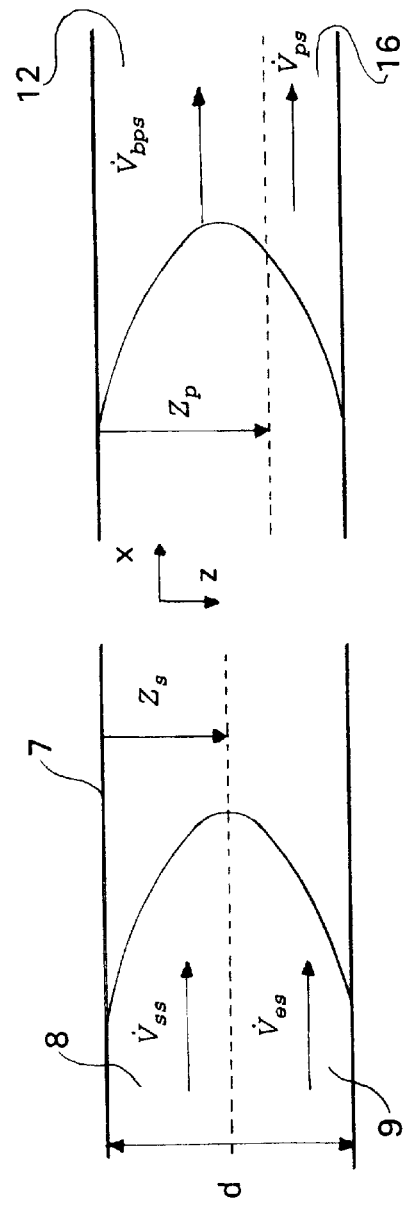
FIG. 7 is a diagram of the entrance and outlet interface streamline in the extraction channel showing the flow rates of the sample, extraction, product and by-product streams.

FIG. 7 shows the extraction channel 7 with laminar extraction stream 9 moving at a velocity $\dot{V}_{es}$, and laminar sample stream 8 moving at a velocity $\dot{V}_{ss}$, and having a stream height, (diffusion direction coordinate) $Z_s$ defining the interface streamline location (dotted line) between the laminar sample stream 8 and the laminar extraction stream 9 near the entrance of the extraction channel 7. The combined height of both streams, and thus the depth of the extraction channel 7, is shown as d. The curved line indicates the shape of the velocity profile. As the streams move along the length of the extraction channel 7, laminar sample stream 8 becomes by-product stream 12 moving with a velocity $\dot{V}_{bps}$ and having a stream height (diffusion direction coordinate) $Z_p$ defining the interface streamline location (dotted line) between the by-product stream 12 and the product stream 13. Laminar extraction stream 9 becomes product stream 16 moving with a velocity $\dot{V}_{ps}$.

Several steps commonly performed in the chemical assay of a fluid mixture are: (1) precise mixture dilution; (2) extraction of a specific constituent; (3) precise mixing of indicator reagents or test probes (e.g. fluorescently tagged polymer beads); and (4) non-invasive detection of the indicator or probe (e.g. absorbance or fluorescence spectroscopy).

Figure 8:
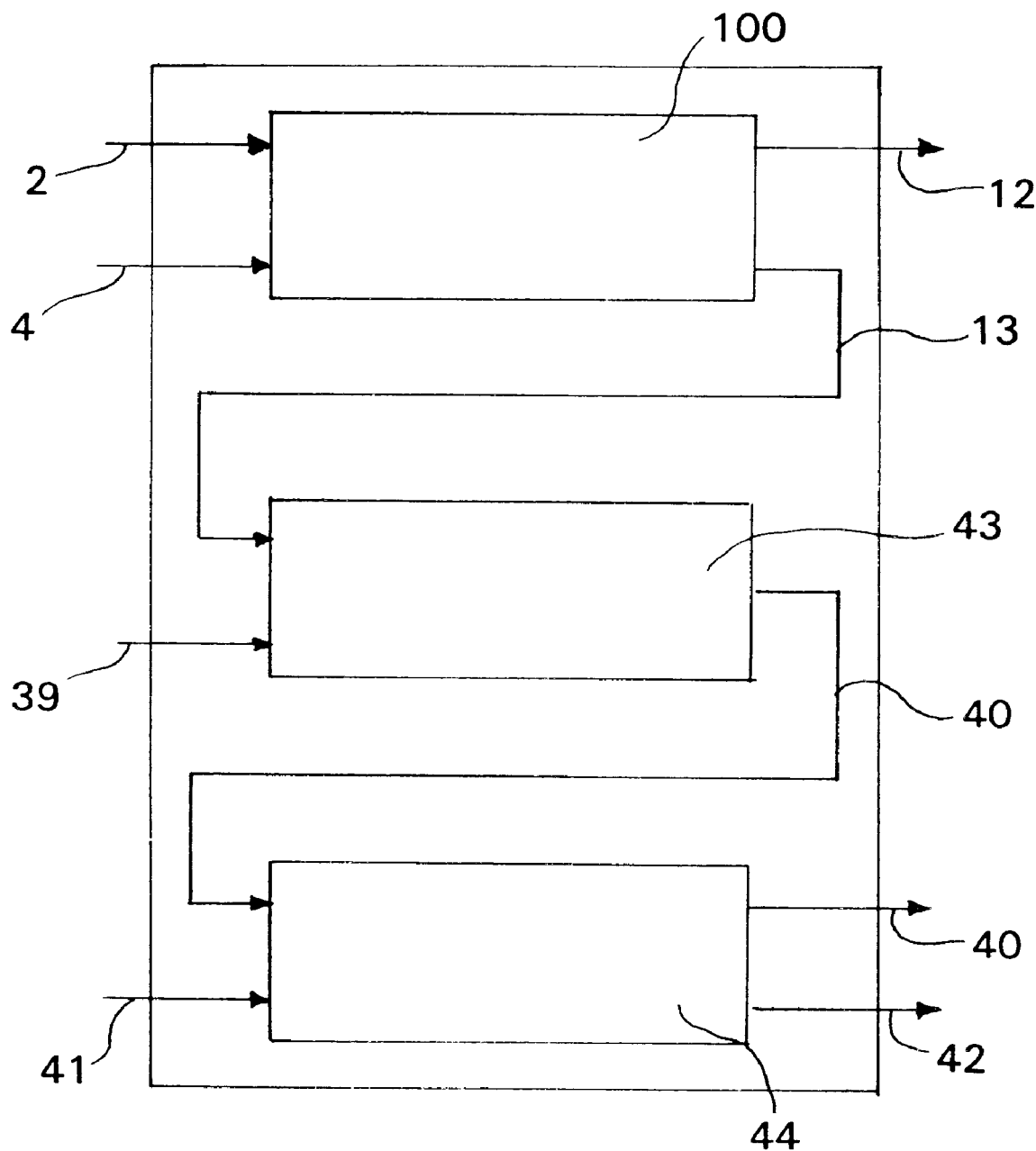
FIG. 8 illustrates the "lab-on-a-chip" concept of this invention for assay of constituents present in a particulate or cell-laden sample stream.

The extraction devices of this invention may be integrated into total analytical systems such as the microfabricated "lab-on-a-chip" illustrated in FIG. 8.

FIG. 8 shows a diffusion-based extraction device 100 of this invention fabricated on a single silicon wafer. A sample stream 2 having a sample stream flow rate $\dot{V}_{ss}$ and a sample stream constituent i concentration $C_{i,ss}$ flows into the diffusion-based extraction device along with an extraction stream 4 having an extraction stream flow rate $\dot{V}_{es}$. By-product stream 12 having a by-product stream flow rate $\dot{V}_{bps}$ and a by-product constituent i concentration $C_{i,bps}$ is removed from the system. Product stream 13 having a product stream flow rate $\dot{V}_{ps}$ and a product stream constituent i concentration $C_{i,ps}$ flows to a diffusion-based mixing device 43 microfabricated onto the same chip. An indicator dye stream 39 having an indicator dye stream flow rate $\dot{V}_{ind}$ and an indicator stream dye concentration $C_{dye,ind}$ also flows into the diffusion-based mixing device 43. Detector stream 40 exits diffusion-based mixing device 43 and flows into detection chamber 44 and optical detection means 41 are actuated to detect a signal, preferably a fluorescence signal 42 while detector stream 40 is in the detection chamber 44. Detector stream 40 then exits detection chamber 44 at a detector stream flow rate $\dot{V}_{ds}$, a detector stream constituent i concentration $C_{i,ds}$ and an indicator dye concentration $C_{dye,ind}$.

The detection strategy presented in FIG. 8 requires constituent extraction from the particulate laden sample, fluorescent indicator mixing with the diluted analyte, and fluorescent optical detection. Critical to the precise operation of the inference technique is the precise regulation of all stream flow rates in the system. Using a calibration between fluorescence intensity and constituent concentration and information precisely defining the constituent extraction and indicator mixing dilution ratios, the concentration of constituent in the original sample stream is estimated. The complete system also includes data reduction, pressure regulation and waste collection. Precise flow control in integrated total analytical systems may in part be achieved using on-chip micro-pumps (Gravesen, P. et al. (1993), "Microfluidics—a review," J. Micromechanics and Microengineering 3(4):168–182; Elwenspoek, M. et al.

(1994), "Towards integrated microliquid handling systems," J. Micromechanics and Microengineering 4(4):227–245; and Forster, F. K. et al. (1995), "Design, Fabrication and Testing of Fixed-Valve Micro-Pumps," ASME International Mechanical Engineering Congress & Exposition, San Francisco, ASME).

In both the "H" design for the extraction system, e.g. FIG. 2 as described in the Example, and the flat extraction system of FIGS. 5 and 6, the diffusing constituents migrate into the extraction stream 4 and tend toward an approximate uniform concentration throughout the extraction channel 7. The sample, extraction, and by-product flow rates are externally regulated, thereby fixing the product stream flow rate. In the design of FIG. 2, fabricated as described in the Example hereof, the channel dimension in the diffusion direction (d), is less than 100 $\mu$m in the Example, and the aspect ratio, defined as the channel dimension normal to the diffusion and flow directions (w) divided by the channel depth (d), is less than 1. In the flat diffusion extraction system of FIGS. 5 and 6, the aspect ratio w/d, where d again is less than about 100 $\mu$m, is greater than 1, but still much less than 50.

The distance required for the constituent being extracted to achieve a concentration throughout the microchannel cross section that is within a fixed percentage of the equilibrium concentration is defined as the equilibration length. The constituent concentration within the microchannel is calculated using a 1-D analytical diffusion model. The equilibration length is used to construct a family of process space design curves specific to the extracted constituent. The optimization objective function is specified to identify the design which maximizes the volume flow rate of product stream within constraints imposed by a system microfabricated on a silicon chip.

The methodology is applied to the design of an optimal device for the extraction of albumin (a protein constituent present in human blood) from a carrier sample stream with viscosity approximately that of water. Whole blood typically has a red blood cell (RBC) content of 40–50% by volume, the RBCs having ellipsoidal shape and 8 $\mu$m major axis dimension, and white blood cells having nominal diameters of approximately 15–25 $\mu$m. In this discussion, the analysis is simplified by considering a single viscosity, single diffusivity process model. Considerations relating to multiple viscosity cases are presented hereinafter. The device presented here is specified for a 1% equilibration length (within 1% of the equilibrium concentration of albumin for an infinite length device). This process sensitivity information provides design requirements for upstream and downstream fluidic components and is essential for integration of the device into a "lab on a chip" chemical analysis system.

A process model is defined by its parameters, physical constants, independent variables, dependent variables, and by the equations used to model the process. The extraction process examined in this paper is illustrated below:

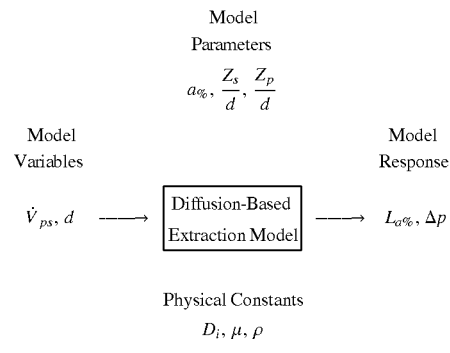

Physical constants cannot be altered with either the design of the device or through its control. There are three physical constants identified above: binary constituent diffusivity, $D_i$; viscosity, $\mu$; and density, $\rho$. The constant parameters are the desired percentage to complete constituent equilibration, $a_\%$, the normalized sample-extraction streamline interface position, $z_s/d$, and the normalized by-product-product streamline interface position, $z_p/d$. The variable model parameters are the product stream flow rate, $\dot{V}_{ps}$, and the diffusion direction channel depth, d. Under this definition the model outputs are the channel length required to achieve $a_\%$, $L_{a\%}$, and the pressure differential across the extraction channel in the direction of flow, $\Delta p$.

A 2-D flow and constituent transport model of the extraction process is presented. The discussion begins by stating the general 3-D transport problem. Simplifying assumptions are then defined for the 2-D approximations and are applied. Solutions to the resulting descriptive modeling equation and associated boundary conditions are then presented for the inviscid flow case and for a numerical solution to the viscous flow case.

General 3-D Mass Transport Model Equation. The general equation describing the transport of a constituent by both diffusive and convective transport is given as (Cussler, E. L. (1984), *Diffusion, Mass Transfer in Fluid Systems*, Cambridge, Cambridge University Press):

$$\frac{\partial c_i}{\partial t} + v_x \frac{\partial c_i}{\partial x} + v_y \frac{\partial c_i}{\partial y} + v_z \frac{\partial c_i}{\partial z} = D_i \left[ \frac{\partial^2 c_i}{\partial x^2} + \frac{\partial^2 c_i}{\partial y^2} + \frac{\partial^2 c_i}{\partial z^2} \right] + r_i \quad (3)$$

where: $c_i$ is the concentration of the $i^{th}$ constituent; $D_i$ is the binary diffusion coefficient for the $i^{th}$ constituent; $v_x$, $v_y$, and $v_z$ are the velocity vector components; and $r_i$ is the rate of production of the $i^{th}$ constituent via chemical reactions in the mixture.

2-D Steady Flow Approximation. The mathematical relations representing the modeling assumptions used in this discussion are presented in Equation 4.

$$\frac{\partial c_i}{\partial t} = 0, \quad \quad 4(a)$$

$$v_y = v_z = 0, \quad \quad 4(b)$$

$$\frac{\partial^2 c_i}{\partial x^2} = \frac{\partial^2 c_i}{\partial y^2} = 0, \quad \quad 4(c)$$

$$r_i = 0 \quad \quad 4(d)$$

Equation 4(a) represents the steady state device operation assumption. The extraction device is intended for dynamic operation but steady state operation is used to target a final configuration design configuration. Flow occurs in a single coordinate direction as reflected in Equation 4(b). Equation 4(c) is justified using two arguments: (1) the spatial scale for diffusion is an order of magnitude smaller in the diffusion extraction direction (z—coordinate) than in the channel flow direction (x—coordinate) (the time required for diffusion over a distance l is proportional to $l^2/D$); (2) diffusion in the channel width direction (y—coordinate) will tend to flatten the concentration profile in the case of viscous flow and cause the solution to more closely approximate diffusion in the invisid flow case with identical mean flow velocities. Equation 4(d) is justified in this discussion because there are no chemical equilibrium kinetics reflecting the change of species in the flow stream for the assays of interest considered here. This is not always the case. Application of Equation 4 to Equation 3 yields the simplified relation, $$\frac{\partial c_i}{\partial x} = \frac{D_i}{v_x}\frac{\partial^2 c_i}{\partial z^2}. \tag{5}$$

Non-dimensional Form. Equation 5 can be normalized with respect to the sample stream constituent concentration and the diffusion channel depth by defining the following non-dimensional change of variables, $$\tilde{c}_i = \frac{c_i}{c_{i,o}}, \tilde{x} = \frac{x}{d}, \tilde{z} = \frac{z}{d}, \tag{6}$$

where: $c_{o,i}$ is the concentration of constituent i in the sample stream, and d is the channel depth. Substitution of Equation 6 into Equation 5 yields $$\frac{\partial \tilde{c}_i}{\partial \tilde{x}} = \left[\frac{D_i}{v_x d}\right]\frac{\partial^2 \tilde{c}_i}{\partial \tilde{z}^2}. \tag{7}$$

The bracketed term in Equation 7 is the inverse of the Peclet number. The Peclet number provides a useful gauge of the relative significance of convective mass transport to diffusion mass transport and is defined as $$Pe = \frac{v_x d}{D_i} \propto \frac{\text{convective transport}}{\text{diffusion transport}}. \tag{8}$$

The concentration is therefore a function of normalized position and the Peclet number,
$\tilde{c}_i(\tilde{x}, \tilde{z}, Pe)$.

Steady Flow Entrance Boundary Condition. The position of the streamline separating the sample and extraction streams at the inlet of the extraction device is $z_s$. The boundary condition at the extraction channel inlet, $\tilde{x}=0$, is unity. The extraction stream normalized concentration is zero, $$\tilde{c}_i(0, \tilde{z}) = \begin{cases} 1, 0 < \tilde{z} < \frac{z_s}{h} \\ 0, \frac{z_s}{h} < \tilde{z} < 1 \end{cases} \tag{9}$$

Infinite Length Channel Far Field Boundary Condition. The far field boundary condition is defined by postulating an infinitely long extraction channel. For such a channel all diffusing constituents must equilibrate across the channel cross-section. Therefore, $$\tilde{c}_i(\infty, \tilde{z}) = \xi \tag{10}$$

where: $\xi$ is the equilibrium normalized concentration. The normalized equilibrium concentration is given as $$\xi = \frac{\dot{V}_{ss}}{\dot{V}_{ss} + \dot{V}_{es}}. \tag{11}$$

Impermeable Channel Wall Boundary Conditions. During steady state operation of the device adsorption of constituents on the device surfaces is assumed to have equilibrated and therefore the mass flux across a control surface defined by the device boundaries is zero. Therefrom from Fick's law the concentration gradient at the boundary must be zero, $$\frac{\partial \tilde{c}_i(\tilde{x}, 0)}{\partial \tilde{z}} = \frac{\partial \tilde{c}_i(\tilde{x}, 1)}{\partial \tilde{z}} = 0. \tag{12}$$

Inviscid Flow (Plug Flow). If inviscid flow is assumed the velocity across the channel in the z-direction will be constant. With this modeling approximation the location of the streamline interface between the sample and extraction steams is given as $$\frac{z_s}{d} = \xi. \tag{13}$$

The solution to Equation 7 subject to the boundary conditions given by Equation 9, Equation 10, and Equation 12 and the streamline interface location (Equation 9) was derived and is given as $$\tilde{c}_i(\tilde{x}, \tilde{z}) = \xi + \sum_{n=1}^{\infty} \frac{2}{\pi(2n-1)} \sin[(2n-1)\pi\xi] \times \tag{14}$$

$$\exp\left[-(2n-1)^2\pi^2\left(\frac{D_i}{v_x d}\right)\tilde{x}\right]\cos[(2n-1)\pi\tilde{z}].$$

Equation 14 was derived using the method of separation of variables. See Folland, G. B. (1992) Fourier Analysis and its Applications, Pacific Grove, Wadsworth & Brooks/Cole Advanced Books and Software, for a detailed presentation of this method and its applications to physical systems.

Viscous Flow—Single Viscosity Fluid. The location of the streamline separating the sample and extraction stream for a viscous flow velocity profile is achieved using conservation of mass. The velocity profile for a single viscosity fluid stream is given as $$v_x(z) = -\frac{d^2}{2\mu}\frac{dP}{dz}\left[\left(\frac{z}{d}\right) - \left(\frac{z}{d}\right)^2\right]. \tag{15}$$

The total volume flow in a channel of depth, d, and width, w, is equal to the sum of the sample and extraction stream flow rates. In terms of the velocity profile this net channel flow rate is given as $$\dot{V}_{ss} + \dot{V}_{es} = w\int_{z=0}^{z=d} v_x(z)dz = -\frac{d^3 b}{12\mu}\frac{dP}{dz} \tag{16}$$

The volume flow rate in the sample stream portion of the extraction channel is given as $$\dot{V}_{ss} = w \int_{z=0}^{z=z_s} v_x(z) dz \tag{17}$$

where $z_s$ is the location of the equilibrium streamline separating the sample and extraction streams. For a viscous flow profile the total sample stream volume flow must reside in the region $0<z<z_s$. Equation 17 may be solved using equations 16 and 15 to yield the cubic relation $$2\left(\frac{z_s}{d}\right)^3 - 2\left(\frac{z_s}{d}\right)^2 + \xi = 0. \tag{18}$$

Any convenient root search technique may be applied to determine the position of the separation streamline separating the sample and extraction streams, $z_s$.

To examine the error associated with assuming inviscid flow a 2-D numerical model was written and used to analyze the flow profile of the "optimal" design suggested by the inviscid flow model. In the numerical simulation model the equation solved is given as $$\frac{\partial^2 \tilde{c}_i}{\partial \tilde{z}^2} = \left[\frac{v_x(\tilde{z})d}{D_i}\right]\frac{\partial \tilde{c}_i}{\partial \tilde{x}}, \tag{19}$$

where the Peclet number is now a function of position within the flow channel due to the viscous flow velocity profile. A centered finite difference in $\tilde{z}$ and upstream difference in $\tilde{x}$ was used to solve the above equation numerically. For $\tilde{z}_s = z_s d = 0.5$ a 20% reduction in the required extraction channel length was observed for identical net channel flow rates. Therefore, using the inviscid assumption to generate design curves should give a conservative calculation of the size of the device required for extraction.

Optimization Objective Function. The goal of this design optimization problem was to maximize the volume flow rate of product stream per unit filter channel breadth, w. The function describing this design object is given as $$\max F(d, L_{a\%}) = \dot{V}_{ps}(d, L_{a\%}). \tag{20}$$

where: d is the channel depth, and $L_{a\%}$ is the $a_\%$ equilibration length. Equation 20 describes the design objective and insures maximum device throughput. In other applications competing design objects may also be considered using a multiobjective design objective function where the competing design objectives are ordered using subjective weights to form the composite multiobjective function. On the microscale, in specific applications, it would be advantageous to maximize the ratio of volume flow rate to unit device volume while simultaneously minimizing the surface area to unit device volume (or equivalently maximizing the volume flow rate to unit surface area) of the micro-fluidic device. These ratios are primarily a function of diffusion direction depth which would directly couple into any device design. In addition, it may also be required that the silicon real estate required to realize the device be simultaneously minimized. For each design objective that must be simultaneously optimized, an additional subjective weight is required. Selection of the appropriate weights will vary from one design configuration to another.

Design Constraints. Because the silicon wafers used to produce the micro-fluidic devices are of finite size, there is a practical limit to the maximum allowable filter length. The $a_\%$ equilibration length, $L_a$, must be less than the maximum practical filter length, $L_{max}$, or $$L_{a-1\%} < L_{max}. \tag{21}$$

Similarly, the channel must be sufficiently deep such that any particulate present in sample and extraction streams will not violate the extraction stream simply due to geometric confinement in the channel, $d>d_{min}$. Further, the channel must not be so deep that the strength of the silicon wafer is excessively compromised, $d<d_{max}$. Combining these two constraints yields the single constraint equation $$d_{min} < d < d_{max}. \tag{22}$$

Finally, the maximum time allowable to complete a set of extraction and subsequent analysis operations will determine a minimum acceptable product stream flow rate for the device. That is, $$\dot{V}_{ps} > \dot{V}_{ps,min}. \tag{23}$$

Figure 9:
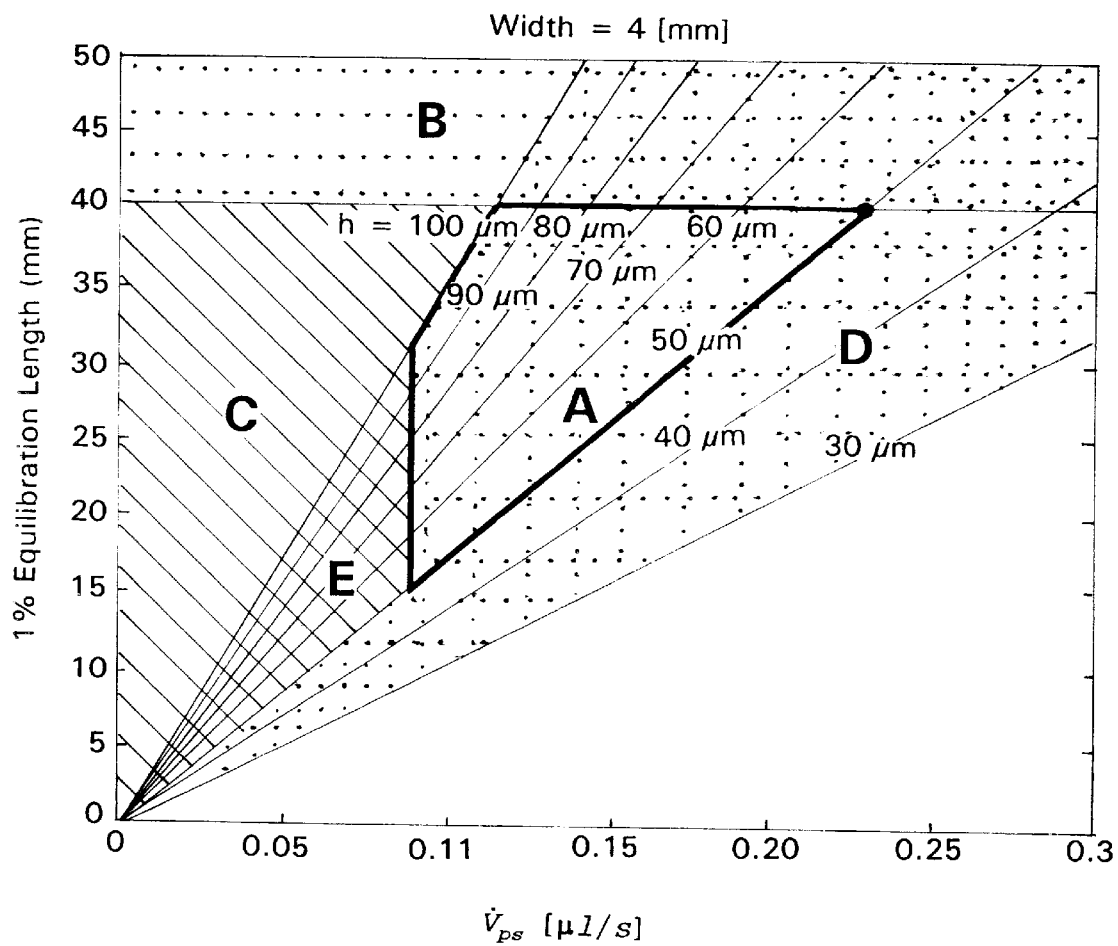
FIG. 9 illustrates optimization of extraction channel length, channel depth and product stream flow rates for a diffusion extraction system microfabricated on a 4 mm wide silicon chip for extracting albumin from carrier fluid having the viscosity of water.
Figure 10:
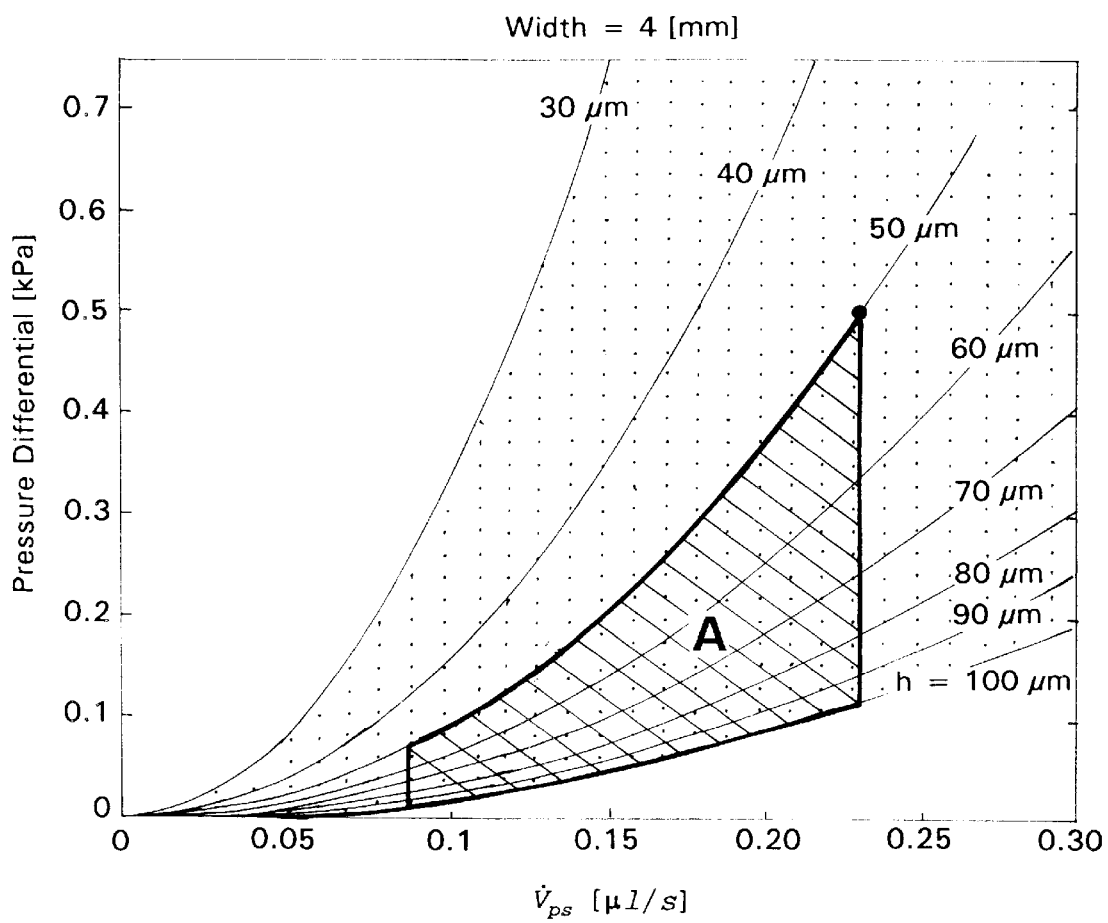
FIG. 10 illustrates optimization of pressure differential, channel depth and product stream flow rates for a diffusion extraction system microfabricated on a 4 mm wide silicon chip for extracting albumin from carrier fluid having the viscosity of water.

FIGS. 9 and 10 present the process space for a family of diffusion extraction devices designed for $a_\% = 1\%$.

FIG. 9 illustrates the design space for a 4 mm wide parallel flow diffusion extraction device to extract albumin from whole blood to achieve a 1% equilibration length, calculated assuming a flow ratio of 1:1 for the sample and extraction stream, and a fluid viscosity of $10^{-3}$ [Pas] and a fluid density of $10^3$ [kg/m$^3$]. The diffusion coefficient for albumin in the saline solution used in this study is $D_{albumin} = 7 \cdot 10^{-11}$ [m$^2$/s].

The physical constants are $D_i = 7 \cdot 10^{-11}$ m$^2$/s (albumin), $\mu = 10^{-3}$ Pa/s (water), and $p = 10^3$ kg/m$^3$ (water). These properties are unvarying for a dilute aqueous solution of albumin. The constants would only change if one were to consider another chemical assay. The parameters chosen as fixed for this design optimization are: $a = 1\%$; $z_s/d = 0.5$; and $w = 4$ mm. These values were chosen as representative for this application and could be varied to achieve specific objectives. For instance, the channel width could be increased to increase the total flow throughput.

In FIG. 9, Area A, illustrates the constrained parameters for the process, with the large black dot at the upper right of this area at a channel length of 40 mm, a channel depth 50 $\mu$m, and a product stream flow rate ($\dot{V}_{ps}$) of about 0.23 $\mu$l/s illustrating the most optimal design. Area B, requiring channel lengths greater than 40 mm, is outside the optimal design because these channel lengths exceed the 40 mm width of the silicon chip (L>$L_{max}$). Area C where the required channel depth is greater than 100 $\mu$m, is outside the optimal design range because the channel depth exceeds that allowable for efficient diffusion (d>$d_{max}$). Area D is outside the optimal design range because the channel is too shallow to pass common cellular constituents (d<$d_{min}$) Area E, where the product stream flow rate 0 to about 0.10 $\mu$l/s is outside the optimal design range because the product flow rate is too small ($Q_{product} < Q_{product,min}$).

FIG. 10 shows the optimal design parameters for conditions as specified in FIG. 9 with respect to the pressure differential across the extraction channel in the direction of flow. Area A, as defined with respect to flow rate and channel depth as described for FIG. 9, is the optimal design area. The large black dot at the upper right of this area again illustrates the most optimal design at a pressure differential of 0.5 kpa.

Equilibration length ($L_{a=1\%}$) is shown to be a linear function of $\dot{V}_{ps}$ at a given channel depth (d). Equation 14 shows the exponential decay of concentration with $\tilde{x}$. Since the diffusivity is a constant for the given constituent of interest, $v_x$, and d control the rate of exponential decay. The factor $1/Pe = D_i/v_x d$ acts like a time constant. If as d is reduced and $v_x$ is increased to compensate with same 1/Pe resulting, then the $La_{a\%=1\%}$ will remain unchanged. As $\dot{V}_{ps}$ increases linearly at a given d, $v_x$ increases proportionately and $L_{a=1\%}$ increases linearly due to the linear reduction in 1/Pe. Convection is becoming more important relative to diffusion and a longer channel length is required to reach equilibrium.

To maximize flow rate at a given equilibrium length, one would be driven to the upper right hand corner of the constrained process space and operate at a small channel depth (FIG. 9) and high pressure differential (FIG. 10). To minimize area requirements, design to operate in the lower left of FIG. 10 at much lower pressure differentials. One should reduce d as far as possible as long as surface effects can be avoided.

In the following discussion, it is assumed that the two fluids being considered have differing viscosities and are homogeneous, immiscible fluids behaving as Newtonian fluids. To model the two-viscosity case and obtain design parameters and results, three separate steps are required. In what follows, the sample stream is identified as region 2 and the extraction stream is identified as region 1. The ratio of absolute viscosity in region 1 to that in region 2 is m, and location of the fluid interface from mid-channel in the direction of region 1 as a fraction of the half-channel width is α. Here the height of the extraction channel is taken as 2ω. The first step is to calculate the velocity profile across both streams in terms of m and α. The second step is to use the velocity profiles to determine the numerical values of α and the ratio of mean velocity of each stream given a volume flow ratio $\dot{V}_{es}/\dot{V}_{ss} \equiv F$. The third step is to solve the diffusion equations based on the location of the inerface, the mean velocites in each stream, and the diffusion coefficent of the particles of interest in each stream.

To accomplish the first step, the Navier-Stokes equations are solved for one-dimensional two-phase fully-developed steady flow of a Newtonian fluid in a rectangular duct to determine the axial velocity profile u(z). The equations in that case reduce to (White, F. M. (1994) Fluid Mechanics):

$$\nabla p + \mu \nabla^2 u = 0. \tag{24}$$

The resulting velocity profile non-dimensionalized by $\omega^2 \Delta p/\mu_1 L$ and with $\tilde{z}=z/\omega$ measured from mid-channel into region 1 is given by $$\tilde{u}_1(\tilde{z}) = \tag{25}$$
$$\frac{1}{2}\left(-\tilde{z}^2 + \frac{\tilde{z}^2(\alpha^2 m - \alpha^2 + 1 - m) - \alpha^2 m + 2m + \alpha^2 - \alpha + m\alpha}{m + m\alpha - \alpha + 1}\right) \alpha < \tilde{z} < 1$$

and $$\tilde{u}_2(\tilde{z}) = \tag{26}$$
$$\frac{1}{2}\left(-m\tilde{z}^2 + \frac{m\tilde{z}(\alpha^2 m - \alpha^2 + 1 - m) + m(\alpha^2 m - \alpha^2 - \alpha + m\alpha + 2)}{m + m\alpha - \alpha + 1}\right) -$$
$$1 < \tilde{z} < \alpha.$$

The second step is to calculate the numerical value of α for a particular value of F by solving for α in the equation $$F = \frac{\int_\alpha^1 \overline{u_1} d\tilde{z}}{\int_{-1}^\alpha \overline{u_2} d\tilde{z}}, \tag{27}$$

and then with that value of α calculate the ratio of mean flows in each region from $$\frac{\overline{U_1}(1-\alpha)}{\overline{U_2}(1+\alpha)} = F. \tag{28}$$

The last step is to solve the diffusion equation (7) in each region subjected to the boundary conditions given by Eqs. (9), (10), and (12) with two additional interface conditions that require continuity of concentration and conservation of mass of the diffusing species at the interface. Now taking $\tilde{z}$ to be measured from the interface into region 1, those conditions are $$\tilde{c}_{i1}(\tilde{x}, 0+) = \tilde{c}_{i2}(\tilde{x}, 0-), \tag{29}$$

and $$D_1 \frac{\partial \tilde{c}_{i1}(\tilde{x}, 0+)}{\partial \tilde{z}} = D_2 \frac{\partial \tilde{c}_{i2}(\tilde{x}, 0+)}{\partial \tilde{z}}. \tag{30}$$

The resulting equation for the mass concentration throughout the channel is given by $$\tilde{c}_i(\tilde{x}, \tilde{z}) = \xi + \sum_{n=1}^{\infty} K_n f_n(\tilde{z}) \exp(-\lambda^2 \tilde{x}/Pe_1) \tag{31}$$

where $\tilde{x}=x/\omega$, the eigenfunctions $f_n(\tilde{z})$ are given by $$f_n(\tilde{z}) = \begin{cases} \cos k\lambda_n \beta_2 \cos \lambda_n(\tilde{z} - \beta_1) & 0 < \tilde{z} < \beta_1 \\ \cos \lambda_n \beta_1 \cos k\lambda_n(\tilde{z} + \beta_2) & -\beta_2 < \tilde{z} < 0 \end{cases}, \tag{32}$$

the eigenvalues $\lambda_n$ are solutions of the characteristic equation $$\tan \lambda_n(\beta_1) + \sigma \tan k\lambda_n(\beta_2) = 0, \tag{33}$$

the constants $K_n$ are given by $$K_n = 4 \frac{-\xi \cos k\lambda_n \beta_2 \sin \lambda_n \beta_1 + (1-\xi)\sigma \cos \lambda_n \beta_1 \sin k\lambda_n \beta_2}{\cos^2 k\lambda_n \beta_2 (\sin 2\lambda_n \beta_1 + 2\lambda_n \beta_1) + \sigma \cos^2 \lambda_n \beta_1 (\sin 2k\lambda_n \beta_2 + 2k\lambda_n \beta_2)} \tag{34}$$

with $\beta_1=1-\alpha$, $\beta_2=1+\alpha$, $k=\sqrt{Pe_2/Pe_1}$, and $\sigma=k(D_2/D_1)$.

Figure 11:
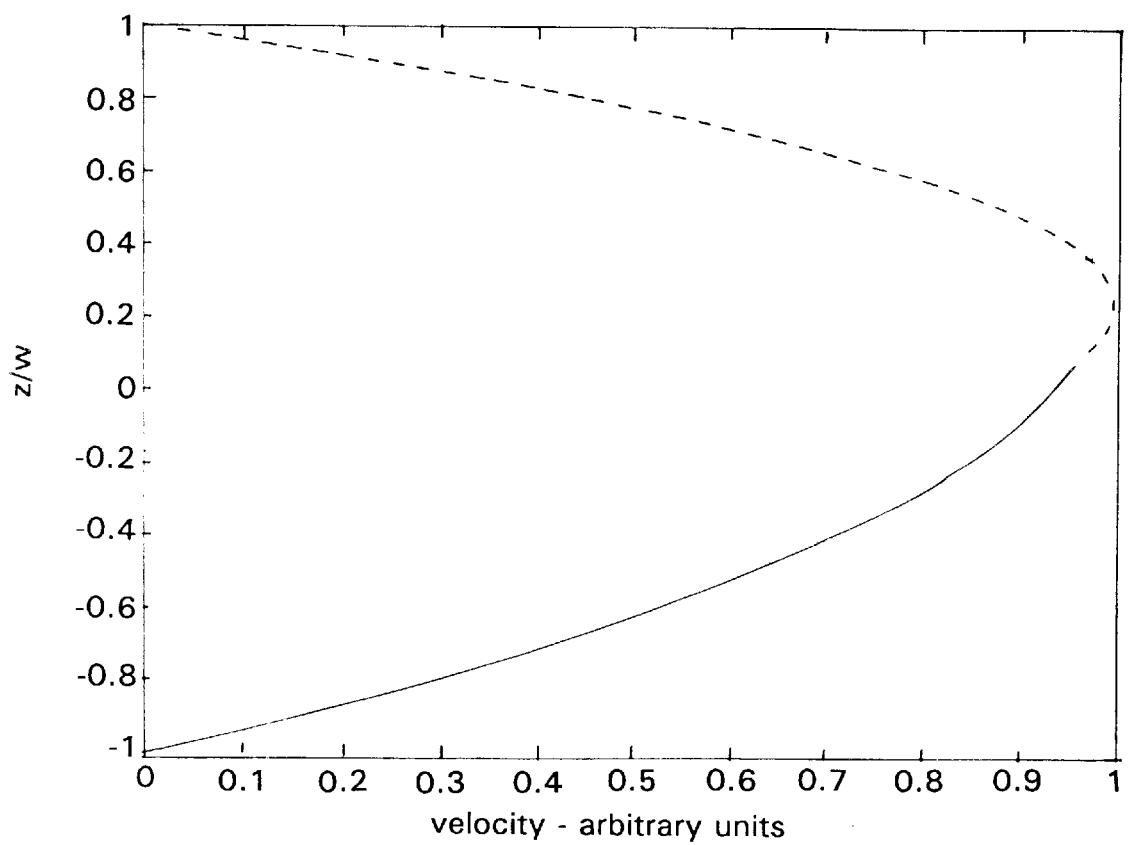
FIG. 11 illustrates the velocity profiles of two homogenous, immiscible fluids behaving as Newtonian fluids but having differing viscosities. The dotted line shows a fluid having the viscosity of water. The solid line shows a fluid having a viscosity three times that of water.
Figure 12:
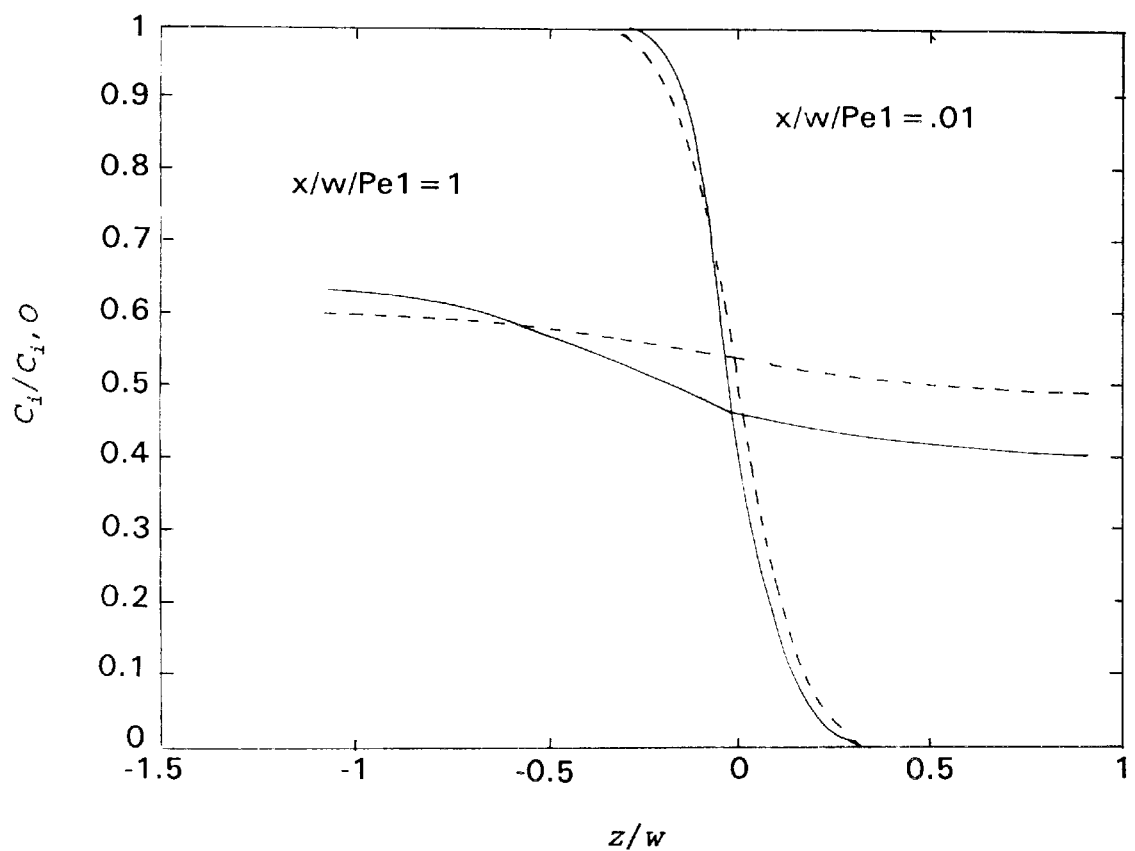
FIG. 12 illustrates a comparison between a two-viscosity model of a diffusion-based extraction system of this invention using the fluids of FIG. 11, and a model assuming the same interface location but with no differences in diffusivity or viscosity in the two fluids.

As an example of the use of the art described above for streams of different viscosity, consider the extraction stream (1) to be water and the sample stream (2) to be a fluid having three times the viscosity of water. Also consider the ratio of volume flow rates to be equal, F=1. Also assume m≈⅓, and $D_2/D_1 \approx$ ½. From the equations above α=0.0960, $\overline{U}_1/\overline{U}_2$=1.21, and the velocity profile across the channel is shown in FIG. 11. In FIG. 12 a comparison is shown between the two-viscosity model of these fluids and one assuming the same interface location, but with no difference in viscosity or diffusivity in each stream. The comparisons in the concentration across the height of the channel are made near the upstream end of the extraction channel (x/w/Pe1=0.01) and also relatively far downstream (x/w/

Pe1=1.0). The two-viscosity calculations are shown as solid lines, and the simpler one-viscosity calculations are shown as dashed lines. Note particularly at the downstream location there is a significant difference between the curves. These results demonstrate the importance of the art as described above for the design and quantitative use of the differential extraction device when used with fluids of different viscosity in each stream.

EXAMPLE

In a preferred process for making a device of this invention, a 1 μm thick wet thermal oxide is grown in a 3" silicon wafer. This oxide is photolithographically patterned with the flow channels and etched to a depth of 60 nm. The wafer is recoated with photoresist and patterned with the through-hole connections. The oxide is completely removed from this pattern. EDP etching is done to etch completely through the wafer (approximately 400 μm). An oxide etch is performed to uniformly remove 400 nm of oxide from the wafer. The flow channels are etched into the silicon approximately 10 μm deep. Finally the wafer is anodically bonded to a 3" disk of Pyrex glass.

The following example demonstrates the use of diffusion based extraction to separate diffusing constituents from a particle laden sample stream using micron sized devices microfabricated in silicon. See FIG. 2. Fluorescein dye was extracted from a sample stream containing 0.5 μm fluorescent polystyrene spheres and fluorescein dye. Operation was demonstrated with zero contamination of the extraction stream by fluorescent spheres. The device had a total extraction channel fluid volume of approximately 1 femtoliter. The example demonstrates that separation is possible at the femtoliter scale given appropriate attention to precise flow stream regulation. Further, it demonstrates that efficient separation is possible in extraction channels with aspect ratios much less than 50 and in channels with diffusion direction dimension much less than 100 μm. The extraction device with w/d<<50, d<100 μm demonstrated the effectiveness of a micro-fluidic system fabricated using silicon microfabrication technology and the essential attributes of ultra-low Reynolds number flow.

A two mask level process was needed to fabricate the device. The first level defined connection ports, which were etched completely through the wafer to the rear side of the silicon. The second level defined the fluid transport channels.

Four-inch chrome masks were made to our specifications by Photo Sciences, Inc. (Torrance, Calif.) and 3" wafers ({100}, n-type) with 500 nm of $SiO_2$ grown on them.

Wafers were cleaned in a Piranha bath ($H_2SO_4$ and $H_2O_2$) (2:1) before processing. A primer (HMDS spun on at 3000 rpm) was used to enhance photoresist adhesion. About one μm of AZ-1370-SF (Hoechst) photoresist was deposited by spin coating (3000 rpm), and this was followed by a soft bake (30 min at 90° C.).

A contact aligner was used to align and expose wafers. Exposure time was varied to yield best results. No post-exposure bake was done. Wafers were developed in AZ-351 (diluted 4:1) (Hoechst) for one minute, and rinsed in DI water. Blue tack tape (Semiconductor Equipment Corporation, Moorpark, Calif.) was applied to the backsides of the wafers to protect the oxide from the oxide etch.

The wafers were immersed in a buffered oxide etch (BOE, 10:1 HF (49%) and $NH_4F$ (10%)) for eleven minutes to completely etch away the unprotected oxide. The blue tack tape was removed by hand, and the photoresist was removed in an acetone rinse.

Silicon etching was done in a mixture of ethylenediamine, pyro-catechol, and water (EPW F-etch) set up in a reflux boiling flask. This etch attacks the {100} planes of silicon at a rate of about 100 μm an hour. Fluid attachment ports were etched in the first step. Flow channels between fluid ports and the filter region were etched in the second step. The barrier was etched in the final step.

After final processing the wafers were once again cleaned in a Piranha bath and rinsed in DI water. They were then diced into individual devices.

We used anodic bonding (Wallis, G. and Pomerantz, D. I. (1969), J. Appl. Physics 40:3946–3949) to attach Pyrex glass to the silicon devices. We obtained 1" square pieces of Pyrex glass (100 μm thickness) from Esco Products Inc. (Oak Ridge, N.J.). First, the silicon and Pyrex glass were immersed in a solution of $H_2O$, $NH_4OH$, and $H_2O$ (1:4:6) heated to 50° C. This process removes any organic matter on the surfaces and also makes the surfaces hydrophilic. After 20 minutes in this solution, the silicon and Pyrex were rinsed with DI water and dried. Anodic bonding was done at 400° C. with 400 V applied between the glass and the silicon.

Fluid connections were made to ports on the back side of the wafer. A glass tube (⅛" inner diameter, about 3 cm long) was epoxied around the fluid ports. The flow was driven by a pressure difference between the entrance ports and the exit port. This pressure difference, less than 3 cm of $H_2O$, is enough to induce a flow velocity of greater than 100 μm per second.

Observations were made on a Zeiss ICM-405 inverted microscope and recorded with a Dage silicon intensified target camera. First, the device was wet with isopropyl alcohol and any trapped air bubbles were removed by applying approximately 70 kPa of pressure. Then a mixture of water, carboxyfluoroscein (Molecular Probes), and 0.5 μm diameter fluorescent balls (Duke Scientific) was introduced into one of the fluid entrance ports. Pure water was introduced at the other entrance port. All the 0.5 μm spheres flowed to the exit channel for the sample stream. The dye diffused throughout the extraction channel and some flows out with the product stream.

The invention has been illustrated with specific embodiments; however, as will be appreciated by those skilled in the art, various substitutions can be made for the specific elements and process steps disclosed herein. The invention is limited only by the scope of the appended claims.

We claim:

1. A microfabricated extraction device for extracting desired particles from a sample stream containing said desired particles comprising:

a. a sample stream inlet;

b. an extraction stream inlet;

c. an extraction channel having an aspect ratio (w/d) less than 50 joining with said sample stream inlet and said extraction stream inlet for receiving a sample stream from said sample stream inlet and an extraction stream from said extraction stream inlet, and forming parallel laminar flow therewith;

d. a by-product stream outlet in fluid communication with said extraction channel for receiving a by-product stream comprising at least a portion of said sample stream from which desired particles have been extracted; and e. a product stream outlet in fluid communication with said extraction channel for receiving a product stream comprising at least a portion of said extraction stream and comprising desired particles extracted from said sample stream;

said device being constructed and arranged such that said parallel laminar flow is preserved throughout said extraction channel.

2. The device of claim 1 wherein said extraction channel has an aspect ratio less than about 25.

3. A method for extraction of at least a portion of desired particles from a sample stream comprising said desired particles and also containing undesired particles, comprising:
   a. introducing said sample stream into the sample stream inlet of a microfabricated extraction device of claim 2;
   b. introducing an extraction stream into the extraction channel of said extraction device;
   c. withdrawing a product stream comprising desired particles from the product stream outlet of said device.

4. The device of claim 1 wherein said extraction channel has an aspect ratio less than about 1.

5. The device of claim 1 fabricated of materials comprising a silicon wafer.

6. The device of claim 1 also comprising means for effecting differential transport of said desired particles from said sample stream into said extraction stream.

7. The device of claim 6 wherein said means for effecting differential transport are means for producing fields selected from the group consisting of magnetic, electrical, dielectrical, sedimentation, shear, centrifugal force, temperature, pressure, and concentration gradient fields.

8. The device of claim 7 wherein said field is a concentration gradient field and wherein said means for producing a concentration gradient field comprises an effectively non-diffusing absorbent or adsorbent material selective for said desired particles in said extraction stream.

9. The device of claim 1 comprising at least one additional product stream outlet.

10. A microfabricated analytical system comprising a device of claim 1 in combination with means for detecting said desired particles in said product stream.

11. The analytical system of claim 10 wherein said means for detecting said desired particles comprise optical sensing means.

12. The analytical system of claim 10 comprising means for mixing said product stream with an indicator substance capable of interacting with said desired particles so as to enable their detection.

13. A microfabricated analytical system comprising a device of claim 1 wherein desired particles are extracted from a sample stream containing desired and undesired particles, which system comprises means for detecting said undesired particles in said product stream.

14. The analytical system of claim 13 wherein said means for detecting said undesired particles comprise optical sensing means.

15. A method for extraction of at least a portion of desired particles from a sample stream comprising said desired particles and also containing undesired particles, comprising:
   a. introducing said sample stream into the sample stream inlet of a microfabricated extraction device of claim 1;
   b. introducing an extraction stream into the extraction channel of said extraction device;
   c. withdrawing a product stream comprising desired particles from the product stream outlet of said device.

16. The method of claim 15 conducted as a continuous process.

17. The method of claim 15 conducted as a batch process.

18. The method of claim 15 wherein a field selected from the group consisting of magnetic, electrical, dielectrical, sedimentation, shear, centrifugal force, temperature gradient, pressure gradient, and concentration gradient fields is produced across said extraction channel to aid in differential transport of desired particles into said extraction stream in said extraction channel.

19. The method of claim 18 wherein said field is a concentration gradient field and said differential transport is effected by diffusion.

20. The method of claim 18 wherein said sample fluid volume is at least about 1 picoliter.

21. The method of claim 18 wherein said sample fluid volume is between about 1 nanoliter and about 10 microliters.

22. The method of claim 18 wherein said sample fluid volume is between about 1 microliter and about 10 microliters.

23. The method of claim 15 wherein the sample and extraction stream have different properties.

24. The method of claim 15 also comprising detecting the presence of said desired particles or said undesired particles in said product stream.

25. The method of claim 15 also comprising determining the concentration of said desired particles or said undesired particles in said product stream.

26. The method of claim 15 also comprising determining the concentration of said desired particles in said sample stream.

27. The method of claim 15 and further comprising detecting the presence and/or concentration of said desired and/or undesired particles in said product stream wherein the presence and/or concentration of said desired and/or undesired particles in said product stream is determined in less than about 1 second after said sample stream is introduced into said sample stream inlet.

28. The method of claim 15 and further comprising detecting the presence and/or concentration of said desired and/or undesired particles in said product stream wherein the presence and/or concentration of said desired and/or undesired particles in said product stream is determined between about 1 second and about 5 minutes after said sample stream is introduced into said sample stream inlet.

29. The method of claim 15 and further comprising detecting the presence and/or concentration of said desired and/or undesired particles in said product stream wherein the presence and/or concentration of said desired and/or undesired particles in said product stream is determined within about 1 to about 4 minutes after said sample stream is introduced into said sample stream inlet.

30. The method of claim 15 wherein said device is flushed to remove both desired and undesired particles after said product stream has been withdrawn, and said extraction method is repeated.

31. The method of claim 15 comprising withdrawing a by-product stream and repeating said method by introducing said by-product stream as sample stream into said sample stream inlet.

32. The method of claim 15 comprising detecting the concentration of a blood component wherein the sample stream comprises whole blood, and particles of a cleaned blood component are extracted into the product stream.

33. The method of claim 15 comprising withdrawing a by-product stream and introducing said by-product stream into a microfabricated flow cytometer.

34. The method of claim 15 comprising withdrawing a product stream and introducing said product stream into a microfabricated flow cytometer.

35. A microfabricated extraction device for extracting desired particles from a sample stream containing said desired particles comprising:
- a. a sample stream inlet;
- b. an extraction stream inlet;
- c. an extraction channel having a depth less than about 100 micrometers joining with said sample stream inlet and said extraction stream inlet for receiving a sample stream from said sample stream inlet and an extraction stream from said extraction stream inlet, and forming parallel laminar flow therewith;
- d. a by-product stream outlet in fluid communication with said extraction channel for receiving a by-product stream comprising at least a portion of said sample stream from which desired particles have been extracted; and
- e. a product stream outlet in fluid communication with said extraction channel for receiving a product stream comprising at least a portion of said extraction stream and comprising desired particles extracted from said sample stream;

said device being constructed and arranged such that said parallel laminar flow is preserved throughout said extraction channel.

36. An analytical system microfabricated on a silicon wafer comprising:
- a. extraction means for extracting desired particles of an analyte comprising:
  - (1) a sample stream inlet;
  - (2) an extraction stream inlet;
  - (3) an extraction channel having an aspect ratio (w/d) less than 50 joining with said sample stream inlet and said extraction stream inlet for receiving a sample stream from said sample stream inlet and an extraction stream from said extraction stream inlet, and forming parallel laminar flow therewith;
  - (4) a by-product stream outlet in fluid communication with said extraction channel for receiving a by-product stream comprising at least a portion of said sample stream from which at least a portion of said desired analyte particles have been extracted; and
  - (5) a product stream outlet in fluid communication with said extraction channel for receiving a product stream comprising at least a portion of said extraction stream and comprising desired analyte particles extracted from said sample stream;
  - (6) said extraction means being constructed and arranged such that said parallel laminar flow is preserved throughout said extraction channel;
- b. a diffusion-based mixing device for mixing said product stream with an indicator substance capable of interacting with said desired analyte particles so as to enable their detection;
- c. a detection chamber wherein the presence of said desired analyte particles may be detected.

37. The analytical system of claim 36 in combination with sensing means whereby the presence of said desired analyte particles in said detection chamber may be detected.

38. The analytical system of claim 37 in combination with quantitation means whereby the concentration of said desired analyte particles in said detection chamber may be measured.

* * * * *

UNITED STATES PATENT AND TRADEMARK OFFICE
CERTIFICATE OF CORRECTION

PATENT NO. : 5,932,100

DATED : August 3, 1999

INVENTOR(S) : Yager et al.

It is certified that error appears in the above-identified patent and that said Letters Patent is hereby corrected as shown below:

In column 12, line 18, please delete "application" and replace with --applications--.

In column 12, lines 33 and 36, please delete "a extraction" and replace with --an extraction--.

In column 12, line 59, please insert --a-- between "from" and "carrier".

In column 13, line 14, please delete "ra" and replace with --$r_a$--.

In column 14, line 56, please delete "with" and replace with --width--.

In claim 23, line 2, delete "stream" and replace with --streams--.

Signed and Sealed this

Third Day of April, 2001

*Attest:*

NICHOLAS P. GODICI

*Attesting Officer*    Acting Director of the United States Patent and Trademark Office